US009109258B2

(12) United States Patent
Steiner et al.

(10) Patent No.: US 9,109,258 B2
(45) Date of Patent: *Aug. 18, 2015

(54) MOLECULAR MARKERS FOR THE DIAGNOSIS AND TREATMENT OF TUMORS

(71) Applicants: Eric Steiner, Wiesbaden (DE); Jan Hengstler, Dortmund (DE); Jens Sagemüller, Greversbroich-Kapellen (DE)

(72) Inventors: Eric Steiner, Wiesbaden (DE); Jan Hengstler, Dortmund (DE); Jens Sagemüller, Greversbroich-Kapellen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/721,374

(22) Filed: Dec. 20, 2012

(65) Prior Publication Data

US 2013/0266936 A1 Oct. 10, 2013

Related U.S. Application Data

(62) Division of application No. 12/086,437, filed as application No. PCT/EP2006/011953 on Dec. 12, 2006, now Pat. No. 8,349,562.

(30) Foreign Application Priority Data

Dec. 12, 2005 (DE) .......................... 10 2005 059 242

(51) Int. Cl.
*C12Q 1/68* (2006.01)
*C07H 21/04* (2006.01)

(52) U.S. Cl.
CPC ........ *C12Q 1/6886* (2013.01); *C12Q 2600/112* (2013.01); *C12Q 2600/118* (2013.01)

(58) Field of Classification Search
None
See application file for complete search history.

(56) References Cited

U.S. PATENT DOCUMENTS

| | | | |
|---|---|---|---|
| 6,228,596 B1 | 5/2001 | Macina et al. | |
| 8,349,562 B2 * | 1/2013 | Steiner et al. | 435/6.11 |
| 2002/0156011 A1 | 10/2002 | Jiang et al. | |
| 2002/0177552 A1 | 11/2002 | Jiang et al. | |
| 2003/0069180 A1 | 4/2003 | Jiang et al. | |
| 2003/0165831 A1 * | 9/2003 | Lee et al. | 435/6 |
| 2003/0165863 A1 | 9/2003 | Chiang | |
| 2004/0259086 A1 * | 12/2004 | Schlegel et al. | 435/6 |
| 2005/0042687 A1 | 2/2005 | Kelly et al. | |
| 2005/0158241 A1 | 7/2005 | Salceda et al. | |
| 2005/0158242 A1 | 7/2005 | Salceda et al. | |
| 2005/0158608 A1 | 7/2005 | Shu et al. | |
| 2006/0078947 A1 | 4/2006 | Kelly et al. | |
| 2007/0037741 A1 | 2/2007 | Baldwin et al. | |
| 2007/0042945 A1 | 2/2007 | Bodary et al. | |
| 2007/0161034 A1 | 7/2007 | Jiang et al. | |
| 2008/0226554 A1 | 9/2008 | Colgan et al. | |

FOREIGN PATENT DOCUMENTS

WO WO 02/081516 A2 10/2002

OTHER PUBLICATIONS

Ronald Thisted. "What is a P-value?" May 25, 1998.*
Cheung, Vivian et al. Natural variation in human gene expression assessed in lymphoblastoid cells. Nature Genetics vol. 33 pp. 422-425, 2003.*
Hoshikawa et al Phystol Genomics, vol. 12, 209-219, (2003).*
Enard et al (Science. Apr. 12, 2002; 296(5566):340-43).*
Matsushita, et al. (FEBS Letters, 1999, vol. 443, pp. 348-352).
Singh, et al. (Glycobiology, 2001, vol. 11, pp. 587-592).
Serra-Pages (The Journal of Biological Chemistry, vol. 273, No. 25, Issue of Jun. 19, pp. 15611-15620, 1998).
Taber's Cyclopedic Medical Dictionary (1985, F.A. Davis Company, Philadelphia, p. 274).
Busken, C., et al. (Digestive Disease Week Abstracts and Itinerary Planner, 2003, Abstract No. 850).
Kaiser (Science, 2006, 313:1370).
Jiang, et al. (J. Biol. Chem., 2003, 278(7) pp. 4763-4769).
Database EMBL Online Accession Q9NPB8; XP-002443978 (Abstract), Oct. 10, 2002.
Database NCBI Online Accession No. AC009173 (Abstract) Mar. 19, 2003.
Database NCBI Online Accession No. BC089418 (Abstract) Oct. 6, 2005.
Database NCBI Online Accession No. CR623938 (Abstract) Jul. 21, 2004.
Database NCBI Online Accession No. AC010401 (Abstract) Mar. 13, 2003.
Database NCBI Online Accession No. NM 019593 (Abstract) Aug. 3, 2005.
Database EMBL Online Accession No. CN 260473; XP-002430975 (Abstract) May 17, 2004.
Database EMBL Online Accession No. DB 027004; XP-002430976 (Abstract) Oct. 21, 2005.
Database EMBL Online Accession No. ADL62788; XP-002443973 (Abstract) Aug. 27, 2010.
Database EMBL Online Accession No. AX340076; XP-002444037 (Abstract) Jan. 10, 2002.
Database EMBL Online Accession No. ABB84606; XP-002444038 (Abstract) Nov. 27, 2005.
Database EMBL Online Accession No. AX675186; XP-002444039 (Abstract) Mar. 27, 2003.
Database EMBL Online Accession No. CQ924942; XP-002444040 (Abstract) Nov. 23, 2004.
Database EMBL Online Accession No. CQ924943; XP-002444041 (Abstract) Aug. 19, 2005.

(Continued)

*Primary Examiner* — Jeanine A Goldberg
(74) *Attorney, Agent, or Firm* — Olson & Cepuritis, Ltd.

(57) ABSTRACT

The invention relates to the diagnosis, prognosis, monitoring, and treatment of neoplastic diseases such as tumor diseases, especially tumor diseases of the endometrium and the metastases thereof.

2 Claims, 7 Drawing Sheets

(56) References Cited

OTHER PUBLICATIONS

Figure 1:
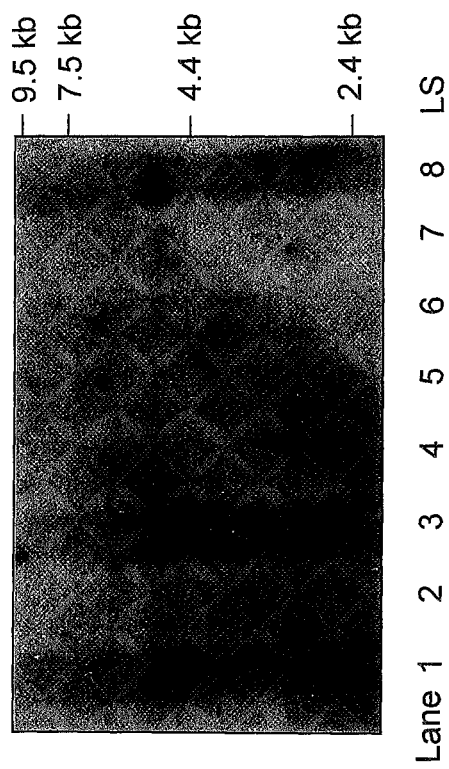

Database EMBL Online Accession No. ADR40144; XP-002443974 (Abstract) Dec. 7, 2010.
Database EMBL Online Accession No. ADR40145; XP-002443975 (Abstract) Dec. 7, 2010.
Database EMBL Online Accession No. ADN05171; XP-002443976 (Abstract) Sep. 15, 2010.
Database EMBL Online Accession No. ADN05172; XP-002443977 (Abstract) Sep. 15, 2010.

* cited by examiner

MOLECULAR MARKERS FOR THE DIAGNOSIS AND TREATMENT OF TUMORS

This application is a division of U.S. Ser. No. 12/086,437 filed Aug. 31, 2009 as a 371 National Stage of PCT/EP2006/011953 filed Dec. 12, 2006, claiming the priority of DE 10 2005 059 242.2 filed Dec. 12, 2005, the entire disclosures of which are incorporated by reference.

INCORPORATION OF SEQUENCE LISTING TEXT FILE

Biological sequence information for this application is included in an ASCII text file having the file name "VOS-207.1-SEQ.txt", created on Dec. 11, 2012, and having a file size of 27,136 bytes, which is incorporated herein by reference.

Cancers are still among the leading causes of death despite interdisciplinary approaches and exhaustive utilization of classical therapy modalities.

Metastasis is one of the most critical factors responsible for the failure of a cancer therapy. Although illustration of protein expression, gene array analysis and determination of critical factors in tumor tissue have improved the prognostic classification of tumors, it is still difficult to predict the risk of metastasis by way of studying the resected primary tumor (Jacquemier J et al., Cancer Res. 65:767-779, 2005; Garber K, Science 303:1754-5, 2004; Hengstler J G et al., Cancer Res. 59, 3206-3214, 1999; Hengstler J G et al., Int. J. Cancer 84, 388-395, 1999; Hengstler J G et al., Int. J. Cancer, 95, 121-127, 2001).

A typical example is cancer of the endometrium, the most common malignancy of the female genital tract. After total resection of the tumor, survival usually depends on the occurrence of metastases. Sites of a recurrence of cancer of the endometrium are paraaortic lymph nodes, bones, lung, pelvis, liver and vagina (Steiner E et al., Int J Gynecol Cancer 13:197-203, 2003). It is currently difficult to predict whether or not a primary tumor of the endometrium has metastasized.

The factors which regulate establishment of the metastatic phenotype are largely undefined. Some histopathological parameters such as tumor stage and histological degree are known to be associated with tumor-free survival (Steiner E et al., Int J Gynecol Cancer 13:197-203, 2003). However, it has been imposBible to predict the risk of metastasis by way of quantifying critical factors in tumor tissue.

It was the object of the present invention to provide targeted structures for a diagnosis, prognosis and therapy of cancers. More specifically, it was the object of the present invention to identify molecular markers which make possible differential diagnosis between metastasizing and non-metastasizing tumors, in particular endometrial tumors.

This object is achieved according to the invention by the subject matter of the claims.

According to the invention, genetic markers are identified whose expression correlates with a metastatic behavior of cancer, in particular cancer of the endometrium. Such genetic markers relate to nucleic acids selected from the group consisting of (a) a nucleic acid which comprises a nucleic acid sequence selected from the group consisting of SEQ ID NO: 1-7, a part of at least 30 consecutive nucleotides thereof and a derivative thereof, (b) a nucleic acid which hybridizes with the nucleic acid of (a) under stringent conditions, (c) a nucleic acid which is degenerated with respect to the nucleic acid of (a) or (b), and (d) a nucleic acid which is complementary to the nucleic acid of (a), (b) or (c). The invention furthermore relates to proteins and peptides encoded by said nucleic acids.

The present invention generally relates to the diagnosis, prognosis, monitoring, i.e. determination, of regression, progression, the course and/or the onset, and to the therapy of neoplastic disorders such as tumor diseases, in particular tumor diseases of the endometrium and metastases thereof.

In one aspect the invention relates to a method of diagnosing and/or monitoring a neoplastic disorder in a patient, comprising (i) detecting and/or determining the amount of a nucleic acid selected from the group consisting of: (a) a nucleic acid which comprises a nucleic acid sequence selected from the group consisting of SEQ ID NO: 1-7, a part of at least 30 consecutive nucleotides thereof and a derivative thereof, (b) a nucleic acid which hybridizes with the nucleic acid of (a) under stringent conditions, (c) a nucleic acid which is degenerated with respect to the nucleic acid of (a) or (b), and (d) a nucleic acid which is complementary to the nucleic acid of (a), (b) or (c), and/or (ii) detecting and/or determining the amount of a protein or peptide encoded by the nucleic acid of (i) or of a part or derivative thereof, and/or (iii) detecting and/or determining the amount of an antibody which is specific to the protein or peptide or part or derivative thereof of (ii), and/or (iv) detecting and/or determining the amount of a T lymphocyte which is specific to the protein or peptide or part or derivative thereof of (ii), where appropriate in a complex with an MHC molecule, in a biological sample isolated from a patient.

In particular embodiments, the patient has a neoplastic disorder, is suspected of suffering from or contracting a neoplastic disorder, or has a risk of a neoplastic disorder. In further embodiments, the patient has metastasis of a neoplastic disorder, is suspected of suffering from or contracting metastasis of a neoplastic disorder or has a risk of metastasis of a neoplastic disorder. In particular embodiments, the patient has undergone or is intended to undergo treatment of a neoplastic disorder, such as treatment by tumor resection, chemotherapy and/or radiotherapy.

Preferably, a presence of the nucleic acid, the protein or peptide or the part or derivative thereof, the antibody and/or the T lymphocyte and/or an increased amount of said nucleic acid, said protein or peptide or said part or derivative thereof, said antibody and/or said T lymphocyte in comparison with a patient without the neoplastic disorder, without a risk of said neoplastic disorder, without metastasis of said neoplastic disorder and/or without a risk of metastasis of said neoplastic disorder indicates the presence of said neoplastic disorder, a risk of said neoplastic disorder, metastasis of said neoplastic disorder and/or a risk of metastasis of said neoplastic disorder.

In a further aspect, the invention relates to a method of evaluating and/or predicting the metastatic behavior and/or the recurrence of a neoplastic disorder, comprising (i) detecting and/or determining the amount of a nucleic acid selected from the group consisting of: (a) a nucleic acid which comprises a nucleic acid sequence selected from the group consisting of SEQ ID NO: 1-7, a part of at least 30 consecutive nucleotides thereof and a derivative thereof, (b) a nucleic acid which hybridizes with the nucleic acid of (a) under stringent conditions, (c) a nucleic acid which is degenerated with respect to the nucleic acid of (a) or (b), and (d) a nucleic acid which is complementary to the nucleic acid of (a), (b) or (c), and/or (ii) detecting and/or determining the amount of a protein or peptide encoded by the nucleic acid of (i) or of a part or derivative thereof, and/or (iii) detecting and/or determining the amount of an antibody which is specific to the protein or peptide or part or derivative thereof of (ii), and/or (iv) detecting and/or determining the amount of a T lymphocyte which is specific to the protein or peptide or part or derivative thereof of (ii), in a biological sample isolated from a patient.

In particular embodiments, the patient has a neoplastic disorder, is suspected of suffering from or contracting a neoplastic disorder, or has a risk of a neoplastic disorder. In further embodiments, the patient has metastasis of a neoplastic disorder, is suspected of suffering from or contracting metastasis of a neoplastic disorder or has a risk of metastasis of a neoplastic disorder. In particular embodiments, the patient has undergone or is intended to undergo treatment of a neoplastic disorder, such as treatment by tumor resection, chemotherapy and/or radiotherapy.

Preferably, a presence of the nucleic acid, the protein or peptide or the part or derivative thereof, the antibody and/or the T lymphocyte and/or an increased amount of said nucleic acid, said protein or peptide or said part or derivative thereof, said antibody and/or said T lymphocyte in comparison with a patient without the neoplastic disorder, without a risk of said neoplastic disorder, without metastasis of said neoplastic disorder, without a risk of metastasis of said neoplastic disorder, without a recurrence of said neoplastic disorder and/or without a risk of a recurrence of said neoplastic disorder indicates the presence of metastasis or recurrence of said neoplastic disorder or a risk of metastasis or recurrence of said neoplastic disorder.

The methods of the invention preferably enable a prognosis to be made on whether metastasis of a neoplastic disorder has occurred or will occur. Preferably, the methods of the invention allow benign and malignant transformations to be distinguished and may provide information on the success of treatment of a neoplastic disorder which has been carried out or is to be carried out, such as treatment by way of tumor resection, chemotherapy and/or radiotherapy. More specifically, the methods of the invention may give information on the probability of a recurrence in a treatment of a neoplastic disorder which has been carried out or is to be carried out.

The skilled worker is familiar with possibilities of detecting and/or determining the amount in the methods of the invention.

In particular embodiments, detection and/or determination of the amount in the methods of the invention comprises (i) contacting the biological sample with an agent which binds specifically to the nucleic acid, to the protein or peptide or the part or derivative thereof, to the antibody or to the T lymphocyte, and (ii) detecting the formation of a complex between said agent and said nucleic acid, said protein or peptide or said part or derivative thereof, said antibody or said T lymphocyte.

A nucleic acid may be detected or the amount of a nucleic acid may be determined according to the invention by using an oligonucleotide or polynucleotide probe which hybridizes specifically with said nucleic acid, or by said nucleic acid being amplified selectively, preferably amplified by polymerase chain reaction. In one embodiment, the probe comprises a sequence of 6-50, in particular 10-30, 15-30 or 20-30, contiguous nucleotides from the nucleic acid to be detected.

A protein or peptide or a part or derivative thereof may be detected or the amount of a protein or peptide or of a part or derivative thereof may be determined according to the invention by using an antibody which binds specifically to said protein or peptide or to said part or derivative thereof.

In one embodiment, the protein or peptide to be detected or the part or derivative thereof is complexed with an MHC molecule.

An antibody may be detected or the amount of an antibody may be determined according to the invention by using a protein or peptide which binds specifically to said antibody.

A T lymphocyte may be detected or the amount thereof may be determined according to the invention by using a cell which presents a complex between a protein or peptide and an MHC molecule to which the T lymphocyte is specific, said cell being preferably an antigen-presenting cell. Where appropriate, a T lymphocyte is detected or the amount thereof is determined by way of detecting its proliferation, cytokine production and/or cytotoxic activity caused by specific stimulation by the complex between the protein or peptide and an MHC molecule. A T lymphocyte may also be detected or the amount thereof may be determined by means of recombinant MHC molecules or complexes of a plurality of MHC molecules loaded with a protein or peptide.

The agent used for detecting or determining the amount, in particular the oligonucleotide or polynucleotide probe, the antibody, the protein or peptide or the cell, are preferably detectably labeled. In particular embodiments, the detectable marker is a radioactive marker, fluorescent marker or enzyme marker.

In a further aspect, the invention relates to a pharmaceutical composition which comprises one or more components selected from the group consisting of (i) a nucleic acid selected from the group consisting of: (a) a nucleic acid which comprises a nucleic acid sequence selected from the group consisting of SEQ ID NO: 1-7, a part of at least 30 consecutive nucleotides thereof and a derivative thereof, (b) a nucleic acid which hybridizes with the nucleic acid of (a) under stringent conditions, (c) a nucleic acid which is degenerated with respect to the nucleic acid of (a) or (b), and (d) a nucleic acid which is complementary to the nucleic acid of (a), (b) or (c), (ii) a protein or peptide encoded by the nucleic acid of (i), a part thereof of at least 8 consecutive amino acids, and a derivative thereof, (iii) an antibody which binds to the protein or peptide or the part or derivative thereof of (ii), (iv) a host cell which expresses the protein or peptide or the part or derivative thereof of (ii), and (v) complexes between the protein or peptide or the part or derivative thereof of (ii) and an MHC molecule.

The one or more components present in the pharmaceutical composition, in particular the nucleic acid and the antibody, preferably recognize a genetic marker identified according to the invention or a protein or peptide encoded by said genetic marker. In a particular embodiment, the nucleic acid present in the pharmaceutical composition of the invention is an antisense nucleic acid which hybridizes with a nucleic acid of a genetic marker identified according to the invention. In another embodiment, the antibody present in a pharmaceutical composition of the invention recognizes a protein or peptide encoded by a genetic marker identified according to the invention and, in a particularly preferred embodiment of the invention, is coupled to a therapeutic or diagnostic agent and/or recruits natural or artificial effector mechanisms, in particular effector mechanisms of an immune reaction, to cells which express a protein or peptide encoded by a genetic marker identified according to the invention.

In another embodiment, administration of a pharmaceutical composition of the invention increases the amount of complexes between an MHC molecule and a protein or peptide encoded by a genetic marker identified according to the invention or a part or derivative thereof. Such an increase in the amount of complexes may be provided by directly administering the latter, where appropriate on the surface of antigen-presenting cells, or by administering a protein or peptide encoded by a genetic marker identified according to the invention or a part or derivative thereof or a nucleic acid coding therefor, where appropriate in a host cell. In particular embodiments, administration of a pharmaceutical composition may induce the death of tumor cells, reduce the growth of tumor cells and/or cause secretion of cytokines.

A nucleic acid may be present in the pharmaceutical composition in an expression vector and functionally linked to a promoter. An antisense nucleic acid present in a pharmaceutical composition of the invention preferably comprises a sequence of 6-50, in particular 10-30, 15-30 or 20-30, contiguous nucleotides.

A host cell present in a pharmaceutical composition of the invention may secrete the protein or peptide or the part or derivative thereof, express said protein or peptide or said part or derivative thereof on the surface or may additionally express an MHC molecule which binds to said protein or peptide or said part or derivative thereof. In one embodiment, the host cell expresses the MHC molecule endogenously. In another embodiment, the host cell expresses the MHC molecule and/or the protein or peptide or the part or derivative thereof in a recombinant manner. The host cell is preferably nonproliferative. In a preferred embodiment, the host cell is an antigen-presenting cell.

An antibody present in a pharmaceutical composition of the invention may be a monoclonal antibody. In other embodiments, the antibody is a chimeric or humanized antibody, a fragment of a natural antibody, or a synthetic antibody. The antibody may be coupled to a therapeutic or diagnostic agent.

A pharmaceutical composition of the invention may comprise a pharmaceutically suitable carrier and/or an adjuvant.

A pharmaceutical composition of the invention is preferably used for treating or diagnosing a neoplastic disorder such as a tumor disease, preferably a tumor disease of the endometrium or metastases thereof. In preferred embodiments the tumor is a metastasizing tumor.

The present invention furthermore relates to a nucleic acid selected from the group consisting of (a) a nucleic acid which comprises a nucleic acid sequence selected from the group consisting of SEQ ID NO: 1-7, a part of at least 30 consecutive nucleotides thereof and a derivative thereof, (b) a nucleic acid which hybridizes with the nucleic acid of (a) under stringent conditions, (c) a nucleic acid which is degenerated with respect to the nucleic acid of (a) or (b), and (d) a nucleic acid which is complementary to the nucleic acid of (a), (b) or (c). The invention furthermore relates to a nucleic acid which codes for a protein or peptide comprising an amino acid sequence selected from the group consisting of SEQ ID NO: 8, a part thereof of at least 8 consecutive amino acids and a derivative thereof.

In a further aspect, the invention relates to a recombinant nucleic acid molecule, in particular DNA or RNA molecule, which comprises a nucleic acid of the invention.

The invention also relates to host cells which contain a nucleic acid of the invention or a recombinant nucleic acid molecule of the invention.

The host cell may further comprise a nucleic acid coding for an MHC molecule. In one embodiment, the host cell expresses the MHC molecule endogenously. In another embodiment, the host cell expresses the MHC molecule and/or the nucleic acid of the invention in a recombinant manner. The host cell is preferably nonproliferative. In a preferred embodiment, the host cell is an antigen-presenting cell.

In a further aspect, the invention relates to a protein or peptide encoded by a nucleic acid selected from the group consisting of (a) a nucleic acid which comprises a nucleic acid sequence selected from the group consisting of SEQ ID NO: 1-7, a part of at least 30 consecutive nucleotides thereof and a derivative thereof, (b) a nucleic acid which hybridizes with the nucleic acid of (a) under stringent conditions, (c) a nucleic acid which is degenerated with respect to the nucleic acid of (a) or (b), and (d) a nucleic acid which is complementary to the nucleic acid of (a), (b) or (c). In a preferred embodiment, the invention relates to a protein or peptide comprising an amino acid sequence selected from the group consisting of SEQ ID NO: 8, a part thereof of at least 8 consecutive amino acids and a derivative thereof.

In a further aspect, the invention relates to an antibody which binds to a protein or peptide of the invention. In further embodiments, the antibody is a chimeric or humanized antibody or a fragment of an antibody. An antibody of the invention may be a polyclonal or monoclonal antibody.

The term "to bind" relates according to the invention to specific binding. "Specific binding" means that binding to a target such an epitope, to which a binding agent such as an antibody is specific, is stronger than binding to a different target. "Stronger binding" may be characterized, for example, by a lower dissociation constant.

The invention furthermore relates to a conjugate between an antibody of the invention and a therapeutic or diagnostic agent. In one embodiment, the therapeutic or diagnostic agent is a toxin.

DETAILED DESCRIPTION OF THE INVENTION

According to the invention, a nucleic acid is preferably deoxyribonucleic acid (DNA) or ribonucleic acid (RNA). According to the invention, nucleic acids comprise genomic DNA, cDNA, mRNA, recombinantly produced and chemically synthesized molecules. A nucleic acid may be present according to the invention as a single-stranded or double-stranded and linear or covalently closed circular molecule.

According to the invention, the term "nucleic acid" also comprises derivatives of nucleic acids. "Derivative" of a nucleic acid means according to the invention that single or multiple, preferably at least 2, at least 4, at least 6, and preferably up to 3, up to 4, up to 5, up to 6, up to 10, up to 15 or up to 20, substitutions, deletions and/or additions of nucleotides are present in the nucleic acid. The term "derivative" of a nucleic acid furthermore also comprises chemical derivatization of a nucleic acid at a nucleotide base, at the sugar or at the phosphate, and nucleic acids containing not naturally occurring nucleotides and nucleotide analogs.

The nucleic acids described according to the invention are preferably isolated. The term "isolated nucleic acid" means according to the invention that the nucleic acid has been (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid available to manipulation by recombinant DNA techniques.

A nucleic acid is "complementary" to another nucleic acid if the two sequences can hybridize with one another and form a stable duplex, said hybridization being carried out preferably under conditions which allow specific hybridization between polynucleotides (stringent conditions). Stringent conditions are described, for example, in Molecular Cloning: A Laboratory Manual, J. Sambrook et al., ed., 2nd edition, Cold Spring Harbor Laboratory Press, Cold Spring Harbor, N.Y. 1989 or Current Protocols in Molecular Biology, F. M. Ausubel et al., ed., John Wiley & Sons, Inc., New York, and refer, for example, to the hybridization at 65° C. in hybridization buffer (3.5×SSC, 0.02% Ficoll, 0.02% polyvinylpyrrolidone, 0.02% bovine serum albumin, 2.5 mM $NaH_2PO_4$ (pH 7), 0.5% SDS, 2 mM EDTA). SSC is 0.15 M sodium chloride/0.15 M sodium citrate, pH 7. After hybridization, the membrane to which the DNA has been transferred, is washed, for example, in 2×SSC at room temperature and then in 0.1-0.5×SSC/0.1×SDS at temperatures up to 68° C.

According to the invention, complementary nucleic acids have at least 40%, in particular at least 50%, at least 60%, at least 70%, at least 80%, at least 90%, and preferably at least 95%, at least 98% or at least 99%, identical nucleotides.

The term "% identity" is intended to refer to a percentage of nucleotides which are identical in an optimal alignment between two sequences to be compared, with said percentage being purely statistical, and the differences between the two sequences may be randomly distributed over the entire length of the sequence and the sequence to be compared may comprise additions or deletions in comparison with the reference sequence, in order to obtain optimal alignment between two sequences. Comparisons of two sequences are usually carried out by comparing said sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, and with the aid of the similarity search algorithm by Pearson and Lipman, 1988, Proc. Natl. Acad. Sci. USA 85, 2444 or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.).

Percentage identity is obtained by determining the number of identical positions in which the sequences to be compared correspond, dividing this number by the number of positions compared and multiplying this result by 100.

For example, the BLAST program "BLAST 2 sequences" which is available on the website http://www.ncbi.nlm.nih.gov/blast/bl2seq/wblast2.cgi may be used.

According to the invention, nucleic acids may be present alone or in combination with other nucleic acids which may be homologous or heterologous. In particular embodiments, a nucleic acid according to the invention is functionally linked to expression control sequences which may be homologous or heterologous with respect to said nucleic acid, with the term "homologous" here referring to the fact that a nucleic acid is also functionally linked naturally to the expression control sequence, and the term "heterologous" referring to the fact that a nucleic acid is not naturally functionally linked to the expression control sequence.

A nucleic acid, preferably a transcribable nucleic acid and in particular a nucleic acid coding for a peptide or protein, and an expression control sequence are "functionally" linked to one another, if they are covalently linked to one another in such a way that transcription or expression of the nucleic acid is under the control or under the influence of the expression control sequence. If the nucleic acid is to be translated into a functional peptide or protein, induction of an expression control sequence when it is functionally linked to the coding sequence results in transcription of said coding sequence, without causing a frame shift in the coding sequence or the coding sequence being unable to be translated into the desired peptide or protein.

The term "expression control sequence" comprises according to the invention promoters, ribosome-binding sequences and other control elements which control transcription of a gene or translation of the derived RNA. In particular embodiments of the invention, the expression control sequences can be regulated. The precise structure of expression control sequences may vary depending on the species or cell type but usually includes 5'-untranscribed and 5'- and 3'-untranslated sequences involved in initiating transcription and translation, respectively, such as TATA box, capping sequence, CAAT sequence and the like. More specifically, 5'-untranscribed expression control sequences include a promoter region which encompasses a promoter sequence for transcription control of the functionally linked nucleic acid. Expression control sequences may also include enhancer sequences or upstream activator sequences.

The term "promoter" or "promoter region" refers to a DNA sequence upstream (5') of the coding sequence of a gene and controls expression of said coding sequence by providing a recognition and binding site for RNA polymerase. The promoter region may include further recognition or binding sites for further factors involved in regulating transcription of said gene. A promoter may control transcription of a prokaryotic or eukaryotic gene. A promoter may be "inducible" and initiate transcription in response to an inducer, or may be "constitutive" if transcription is not controlled by an inducer. An inducible promoter is expressed only to a very small extent or not at all, if an inducer is absent. In the presence of the inducer, the gene is "switched on" or the level of transcription is increased. This is usually mediated by binding of a specific transcription factor.

Examples of promoters preferred according to the invention are promoters for SP6, T3 or T7 polymerase.

According to the invention, the term "expression" is used in its most general meaning and comprises production of RNA or of RNA and protein. It also comprises partial expression of nucleic acids. Furthermore, expression may be transient or stable. With respect to RNA, the term "expression" or "translation" refers in particular to production of peptides or proteins.

Furthermore, a nucleic acid coding for a protein or peptide may according to the invention be linked to another nucleic acid coding for a peptide sequence which controls secretion of the protein or peptide encoded by said nucleic acid from a host cell. According to the invention, a nucleic acid may also be linked to another nucleic acid coding for a peptide sequence which causes anchoring of the encoded protein or peptide to the cell membrane of a host cell or compartmentalization thereof into particular organelles of said cell. Similarly, a linkage to a nucleic acid representing a reporter gene or any "tag" may be established.

In a preferred embodiment, a nucleic acid is present according to the invention in a vector, where appropriate with a promoter controlling expression of said nucleic acid. The term "vector" is used here in its most general meaning and comprises any intermediate vehicles for a nucleic acid which, for example, enable said nucleic acid to be introduced into prokaryotic and/or eukaryotic cells and, where appropriate, to be integrated into a genome. Such vectors are preferably replicated and/or expressed in the cell. Vectors comprise plasmids, phagemids or viral genomes. The term "plasmid", as used herein, generally relates to a construct of extrachromosomal genetic material, usually a circular DNA duplex, which can replicate independently of chromosomal DNA.

According to the invention, the term "host cell" refers to any cell which can be transformed or transfected with an exogenous nucleic acid, preferably DNA or RNA. The term "host cell" comprises according to the invention prokaryotic (e.g. *E. coli*) or eukaryotic cells (e.g. mammalian cells, in particular cells from humans, yeast cells and insect cells). Particular preference is given to mammalian cells such as cells from humans, mice, hamsters, pigs, goats and primates. The cells may be derived from a multiplicity of tissue types and comprise primary cells and cell lines. Specific examples include keratinocytes, peripheral blood leukocytes, bone marrow stem cells and embryonic stem cells. In other embodiments, the host cell is an antigen-presenting cell, the term "antigen-presenting cell" comprising according to the invention dendritic cells, monocytes and macrophages. A nucleic acid may be present in the host cell in a single or in several copies and, in one embodiment, is expressed in the host cell.

In those cases of the invention, in which an MHC molecule presents a protein or peptide, an expression vector may also comprise a nucleic acid sequence coding for said MHC molecule. The nucleic acid sequence coding for the MHC molecule may be present on the same expression vector as the nucleic acid coding for the protein or peptide, or both nucleic acids may be present on different expression vectors. In the latter case, the two expression vectors may be cotransfected into one cell. If a host cell expresses neither the protein or peptide nor the MHC molecule, both nucleic acids coding therefor may be transfected into the cell either on the same expression vector or on different expression vectors. If the cell already expresses the MHC molecule, only the nucleic acid sequence coding for the protein or peptide may be transfected into the cell.

The invention also comprises kits for amplifying a nucleic acid in order to detect thereby said nucleic acid or determine its amount. Such kits comprise, for example, a pair of amplification primers which hybridize to the nucleic acid to be amplified. The primers preferably comprise a sequence of from 6-50, in particular 10-30, 15-30 or 20-30, contiguous nucleotides of the nucleic acid to be amplified and do not overlap in order to avoid formation of primer dimers. One of said primers will hybridize to a strand of the nucleic acid to be amplified and the other primer will hybridize to the complementary strand in an arrangement which allows amplification of the nucleic acid.

"Antisense nucleic acids" may be used for regulating, in particular reducing, expression of a nucleic acid. The term "antisense nucleic acid" means according to the invention an oligonucleotide which is an oligoribonucleotide, oligodeoxyribonucleotide, modified oligoribonucleotide or modified oligodeoxyribonucleotide and which hybridizes under physiological conditions to DNA comprising a particular gene or to mRNA of said gene, thereby inhibiting transcription of said gene and/or translation of said mRNA. An "antisense nucleic acid" comprises according to the invention also a construct which contains a nucleic acid or part thereof in reverse orientation with respect to its natural promoter. An antisense transcript of a nucleic acid or of a part thereof may form a duplex with the naturally occurring mRNA which specifies a peptide or protein, thus preventing translation of said mRNA into said peptide or protein. Another option is the use of ribozymes for inactivating a nucleic acid. Preferred antisense oligonucleotides of the invention have a sequence of 6-50, in particular 10-30, 15-30 or 20-30, contiguous nucleotides of the target nucleic acid and are preferably fully complementary to said target nucleic acid or a part thereof.

In preferred embodiments, the antisense oligonucleotide hybridizes with an N-terminal or 5' upstream site such as a translation initiation site, transcription initiation site or promoter site. In other embodiments, the antisense oligonucleotide hybridizes to a 3'-untranslated region or mRNA splicing site.

In one embodiment, an oligonucleotide according to the invention consists of ribonucleotides, deoxyribonucleotides or a combination thereof. The 5' end of a nucleotide and the 3' end of another nucleotide are linked here via phosphodiester bond. These oligonucleotides may be synthesized in the usual manner or produced recombinantly.

In preferred embodiments, an oligonucleotide of the invention is a "modified" oligonucleotide. Said oligonucleotide may be modified in very different ways, for example in order to increase its stability or therapeutic efficacy, without impeding its ability to bind to its target. The term "modified oligonucleotide" means according to the invention an oligonucleotide in which (i) at least two of its nucleotides are linked to one another by a synthetic internucleoside bond (i.e. an internucleoside bond that is not a phosphodiester bond), and/or (ii) a chemical group which is normally not present in nucleic acids is covalently linked to the oligonucleotide. Preferred synthetic internucleoside bonds are phosphorothioates, alkyl phosphonates, phosphorodithioates, phosphate esters, alkyl phosphonothioates, phosphoramidates, carbamates, carbonates, phosphate triesters, acetamidates, carboxymethyl esters and peptides.

The term "modified oligonucleotide" also comprises oligonucleotides having one or more covalently modified bases and/or one or more covalently modified sugars. Examples of "modified oligonucleotides" include oligonucleotides containing sugar residues which are covalently bound to low molecular weight organic groups other than a hydroxyl group in the 3' position and a phosphate group in the 5' position. Modified oligonucleotides may comprise, for example, a 2'-O-alkylated ribose residue or a sugar other than ribose, such as arabinose.

The term "peptide" relates to substances which comprise at least two, at least 3, at least 4, at least 6, at least 8, at least 10, at least 13, at least 16, at least 20 and preferably up to 50, 100 or 150, consecutive amino acids which are linked to one another via peptide bonds. The term "protein" relates to large peptides, preferably peptides with at least 151 amino acids, but the terms "peptide" and "protein" are used herein generally as synonyms.

The proteins and peptides described according to the invention are preferably isolated. The terms "isolated protein" or "isolated peptide" mean that the protein or peptide is separated from its natural environment. An isolated protein or peptide may be in an essentially purified state. The term "essentially purified" means that the protein or peptide is essentially free of other substances with which it is associated in nature or in vivo.

Such proteins and peptides are used, for example, in production of antibodies and can be employed in an immunological or diagnostic assay or as therapeutics. Proteins and peptides described according to the invention may be isolated from biological samples such as tissue homogenates or cell homogenates and may also be expressed recombinantly in a multiplicity of prokaryotic or eukaryotic expression systems.

"Derivatives" of a protein or peptide or of an amino acid sequence in accordance with the present invention include amino acid insertion variants, amino acid deletion variants and/or amino acid substitution variants.

Amino acid insertion variants include amino- and/or carboxy-terminal fusions, and insertions of single or multiple amino acids in a particular amino acid sequence. In amino acid sequence variants with an insertion, one or more amino acid residues are introduced into a predetermined site in an amino acid sequence, although random insertion with suitable screening of the resulting product is also possible. Amino acid deletion variants are characterized by the removal of one or more amino acids from the sequence. Amino acid substitution variants are distinguished by at least one residue in the sequence being removed and another residue being inserted in its place. The modifications are preferably present at positions in the amino acid sequence which are not conserved between homologous proteins or peptides and/or amino acids are preferably replaced by others having similar properties such as hydrophobicity, hydrophilicity, electronegativity, volume of the side chain and the like (conservative substitution). Conservative substitutions relate for example to replacement of one amino acid with another amino acid which is listed below in the same group as the substituted amino acid:
1. Small aliphatic, nonpolar or slightly polar residues: Ala, Ser, Thr (Pro, Gly)
2. Negatively charged residues and their amides: Asn, Asp, Glu, Gln
3. Positively charged residues: His, Arg, Lys
4. Large aliphatic, nonpolar residues: Met, Leu, Ile, Val (Cys)
5. Large aromatic residues: Phe, Tyr, Trp.

Three residues are put in parentheses due to their particular role in protein architecture. Gly is the only residue without a side chain and thus confers flexibility on said chain. Pro has an unusual geometry which greatly restricts the chain. Cys can form a disulfide bridge.

The amino acid variants described above can easily be prepared with the aid of known peptide synthesis techniques such as, for example, by "Solid phase synthesis" (Merrifield, 1964) and similar methods or by recombinant DNA manipulation. The manipulation of DNA sequences for preparing proteins and peptides with substitutions, insertions or deletions is described in detail in Sambrook et al. (1989), for example.

According to the invention, "derivatives" of proteins or peptides also include single or multiple substitutions, deletions and/or additions of any molecules which are associated with the protein or peptide, such as carbohydrates, lipids and/or proteins or peptides. The term "derivative" furthermore also extends to all functional chemical equivalents of said proteins and peptides and to substances containing not only amino acid components but also non-amino acid components such as sugars and phosphate structures, and also include substances containing bonds such as ester bonds, thioether bonds or disulfide bonds.

A part or fragment of a protein or peptide has according to the invention preferably a functional property of the protein or peptide from which it is derived. Such functional properties include, for example, the interaction with antibodies or the interaction with other peptides or proteins. An important property is the ability to form a complex with MHC molecules and, where appropriate, to generate an immune reaction, for example by stimulating cytotoxic or helper T cells. A part or fragment of a protein comprises according to the invention preferably a sequence of at least 6, at least 8, at least 10, at least 12, at least 15, at least 20, or at least 30, and preferably up to 8, 10, 12, 15, 20, 30 or 50, consecutive amino acids of said protein or peptide.

A part or a fragment of a nucleic acid coding for a protein or peptide relates according to the invention preferably to that part of the nucleic acid which codes at least for the protein or peptide and/or for a part or a fragment of said protein or peptide, as defined above.

Antisera containing antibodies which bind specifically to a target may be produced by various standard methods; cf., for example, "Monoclonal Antibodies: A Practical Approach" by Philip Shepherd, Christopher Dean ISBN 0-19-963722-9, "Antibodies: A Laboratory Manual" by Ed Harlow, David Lane ISBN: 0879693142 and "Using Antibodies: A Laboratory Manual: Portable Protocol NO" by Edward Harlow, David Lane, Ed Harlow ISBN: 0879695447. It is also possible here to generate antibodies having affinity and specificity which recognize complex membrane proteins in their native form (Azorsa et al., *J. Immunol. Methods* 229: 35-48, 1999; Anderson et al., *J. Immunol.* 143: 1899-1904, 1989; Gardsvoll, *J. Immunol. Methods* 234: 107-116, 2000). This is especially important to the production of antibodies which are intended to be used therapeutically, but also to many diagnostic applications. This may involve immunization with the complete protein, with extracellular subsequences, as well as with cells which express the target molecule in a physiologically folded form.

Monoclonal antibodies are traditionally produced with the aid of the hybridoma technology (technical details: see "Monoclonal Antibodies: A Practical Approach" by Philip Shepherd, Christopher Dean ISBN 0-19-963722-9; "Antibodies: A Laboratory Manual" by Ed Harlow, David Lane ISBN: 0879693142, "Using Antibodies: A Laboratory Manual: Portable Protocol NO" by Edward Harlow, David Lane, Ed Harlow ISBN: 0879695447).

It is known that only a small part of an antibody molecule, the paratope, is involved in binding of the antibody to its epitope (cf. Clark, W. R. (1986), *The Experimental Foundations of Modern Immunology*, Wiley & Sons, Inc., New York; Roitt, I. (1991), *Essential Immunology*, 7th edition, Blackwell Scientific Publications, Oxford). The pFc' and Fc regions, for example, are effectors of the complement cascade but they are not involved in antigen binding. An antibody from which the pFc' region has been enzymatically removed or which has been produced without the pFc' region, referred to as F(ab')$_2$ fragment, carries both antigen binding sites of a complete antibody.

Similarly, an antibody from which the Fc region has been enzymatically removed or which has been produced without the Fc region, referred to as Fab fragment, carries one antigen binding site of an intact antibody molecule. Furthermore, Fab fragments consist of a covalently bound light chain of an antibody and part of the heavy chain of said antibody, referred to as Fd. The Fd fragments are the major determinants of antibody specificity (a single Fd fragment may be associated with up to ten different light chains, without altering specificity of the antibody), and Fd fragments when isolated retain the ability to bind to an epitope.

Within the antigen-binding part of an antibody, there are complementarity-determining regions (CDRs) which directly interact with the epitope of the antigen, and framework regions (FRs) which maintain the tertiary structure of the paratope. Both the Fd fragment of the heavy chain and the light chain of IgG immunoglobulins contain four framework regions (FR1 to FR4) which are separated in each case by three complementarity-determining regions (CDR1 to CDR3). The CDRs and in particular CDR3 regions and even more the CDR3 region of the heavy chain are largely responsible for antibody specificity.

It is known that non-CDR regions of a mammalian antibody can be replaced with similar regions of antibodies having the same or a different specificity, with the specificity to the epitope of the original antibody being retained. This made it possible to develop "humanized" antibodies in which non-human CDRs are covalently linked to human FR and/or Fc/pFc' regions to produce a functional antibody.

A different example is described in WO 92/04381 by way of producing and using humanized murine RSV antibodies in which at least part of the murine FR regions have been replaced with FR regions of human origin. Such antibodies, including fragments of intact antibodies with antigen binding capability, are frequently referred to as "chimeric" antibodies.

According to the invention, the term "antibody" also includes F(ab')₂, Fab, Fv and Fd antibody fragments, chimeric antibodies in which the Fc and/or FR and/or CDR1 and/or CDR2 and/or light chain CDR3 regions have been replaced with homologous human or nonhuman sequences, chimeric F(ab')₂ fragment antibodies in which the FR and/or CDR1 and/or CDR2 and/or light chain CDR3 regions have been replaced with homologous human or nonhuman sequences, chimeric Fab fragment antibodies in which the FR and/or CDR1 and/or CDR2 and/or light chain CDR3 regions have been replaced with homologous human or nonhuman sequences and chimeric Fd fragment antibodies in which the FR and/or CDR1 and/or CDR2 regions have been replaced with homologous human or nonhuman sequences. According to the invention, the term "antibody" also comprises single-chain antibodies.

Antibodies may also be coupled to specific diagnostic agents in order to display, for example, cells and tissues which express particular proteins or peptides. They may also be coupled to therapeutic agents.

Diagnostic agents include any labeling which is suitable for: (i) providing a detectable signal, (ii) interacting with a second label in order to modify the detectable signal provided by the first or second label, for example FRET (fluorescence resonance energy transfer), (iii) influencing mobility such as electrophoretic mobility by means of charge, hydrophobicity, form or other physical parameters, or (iv) providing a capture group, for example affinity complexing, antibody/antigen complexing or ionic complexing. Suitable labels are structures such as fluorescent labels, luminescent labels, chromophore labels, radioisotopic labels, isotopic labels, preferably stable isotopic labels, enzyme labels, particle labels, in particular metal particle labels, magnetic particle labels, polymeric particle labels, small organic molecules such as biotin, ligands of receptors or binding molecules such as cell adhesion proteins or lectins, and labeling sequences comprising nucleic acid and/or amino acid sequences. Diagnostic agents include, but are not limited to, barium sulfate, iocetamic acid, iopanoic acid, calcium ipodate, sodium diatrizoate, meglumine diatrizoate, metrizamide, sodium tyropanoate and radio diagnostic agents, including positron emitters such as fluorine-18 and carbon-11, gamma emitters such as iodine-123, technetium-99m, iodine-131 and indium-111, and nuclides for nuclear magnetic resonance, such as fluorine and gadolinium.

The term "therapeutic agent" means according to the invention any substance capable of exerting a therapeutic action, and includes, but is not limited to, anticancer agents, compounds provided with radioactive iodine, toxins, cytostatic or cytolytic drugs, etc. Anticancer agents include, for example, aminoglutethimide, azathioprine, bleomycin sulfate, busulfan, carmustine, chlorambucil, cisplatin, cyclophosphamide, cyclosporin, cytarabidine, dacarbazine, dactinomycin, daunorubin, doxorubicin, taxol, etoposide, fluoruracil, interferon-α, lomustine, mercaptopurine, methotrexate, mitotane, procarbazine HCl, thioguanine, vinblastine sulfate and vincristine sulfate. Further anticancer agents are described, for example, in Goodman and Gilman, "The Pharmacological Basis of Therapeutics", 8th edition, 1990, McGraw-Hill, Inc., especially chapter 52 (Antineoplastic Agents (Paul Calabresi and Bruce A. Chabner)). Toxins may be proteins such as pokeweed antiviral protein, cholera toxin, pertussis toxin, ricin, gelonin, abrin, diphtheria exotoxin, or *Pseudomonas* exotoxin. Toxin residues may also be high energy-emitting radionuclides such as cobalt-60.

The term "major histocompatibility complex" or "MHC" relates to a complex of genes that is present in all vertebrates. MHC proteins or molecules are involved in the signaling between lymphocytes and antigen-presenting cells in normal immune reactions, wherein they bind peptides and present them for recognition by T cell receptors. MHC molecules bind peptides within an intracellular processing compartment and present said peptides on the surface of antigen-presenting cells for recognition by T cells. The human MHC region, also referred to as HLA, is located on chromosome 6 and comprises the class I and class II regions. In a preferred embodiment according to all aspects of the invention, an MHC molecule is an HLA molecule.

The term "patient" includes according to the invention male and female patients, preferably female patients. Examples of patients include according to the invention humans, nonhuman primates or other animals, in particular mammals such as cows, horses, pigs, sheep, goats, dogs, cats or rodents such as mice and rats. In a particularly preferred embodiment, the patient is a human being.

According to the invention, the term "neoplastic disorder" relates to de novo formation of body tissues in the sense of disregulated, uncontrolled and/or autonomous excess growth, with the term "disorder" relating to any pathological state. Preference is given to a neoplastic disorder being according to the invention a tumor disease or cancer such as leukemias, seminomas, melanomas, teratomas, glyomas, cancers of the kidney, adrenal gland, thyroid, intestine, liver, colon, stomach, gastrointestinal tract, lymph nodes, esophagus, colorectum, pancreas, ear, nose and throat (ENT), breast, prostata, uterus, ovaries, bones, vagina and lung, and in particular cancer of the endometrium and metastases thereof which in the case of cancer of the endometrium, occur, in particular, in paraaortic lymph nodes, bones, lung, pelvis, liver and vagina. In a preferred embodiment, a neoplastic disorder is induced according to the invention by carcinogenesis. According to the invention, neoplasias relate to benign changes without metastasis and malignant changes, in particular with invasive growth and the formation of metastases.

According to the invention, the term "myometrium" relates to the strong middle layer of the uterine wall, formed by smooth muscles.

The term "recurrence" relates according to the invention to a relapse of a disease, in particular its recurrence after healing or apparent healing. With respect to a tumor disease, the term "recurrence" relates to the recurrence of tumors after initially successful treatment such as treatment by surgery, chemotherapy and/or radiotherapy.

The term "increased amount" preferably relates to an increase by at least 10%, in particular at least 20%, at least 50% or at least 100%. The amount of a substance is increased in a test specimen such as a biological sample with respect to a reference, even if said substance is detectable in the test specimen but is not present and/or not detectable in the reference.

According to the invention, a biological sample may be a tissue sample, including bodily fluids, and/or a cellular sample, and may be obtained in the usual manner such as by tissue biopsy, including punch biopsy, and by taking blood, bronchial aspirate, sputum, urine, feces or other bodily fluids.

The terms "T cell" and "T lymphocyte" include T helper cells and cytolytic or cytotoxic T cells.

Some therapeutic methods rely on a response of the immune system of a patient, which results in the lysis of antigen-presenting cells such as cancer cells presenting one or more peptides. This involves, for example, administering autologous cytotoxic T lymphocytes which are specific to a complex of a peptide and an MHC molecule to a patient having a cellular anomaly. In vitro production of such cytotoxic T lymphocytes has been disclosed.

In this connection, the invention relates to a therapeutic method which is referred to as adoptive transfer (Greenberg, *J. Immunol.* 136(5):1917, 1986; Riddel et al., *Science* 257: 238, 1992; Lynch et al., *Eur. J. Immunol.* 21:1403-1410, 1991; Kast et al., *Cell* 59:603-614, 1989). This involves combining cells which present the desired complex (e.g. dendritic cells) with cytotoxic T lymphocytes of the patient to be treated, resulting in propagation of specific cytotoxic T lymphocytes. The propagated cytotoxic T lymphocytes are then administered to a patient having a cellular anomaly, with the anomalous cells presenting the specific complex. The cytotoxic T lymphocytes then lyse the anomalous cells, thereby achieving a desired therapeutic action.

Adoptive transfer is not the only form of therapy which can be applied according to the invention. Cytotoxic T lymphocytes may also be generated in vivo in a manner known per se. One method comprises using nonproliferative cells expressing the complex, such as irradiated tumor cells or cells which have been transfected with one or both genes necessary for presentation of the complex (i.e. the antigenic peptide and the presenting MHC molecule). A preferred form is that of introducing a protein or peptide which is characteristic for a tumor, in the form of recombinant RNA, into cells which then present the complex of interest. Such cells are recognized by autologous cytotoxic T lymphocytes which then propagate.

A similar action can be achieved by combining a protein or peptide with an adjuvant in order to make possible in vivo incorporation into antigen-presenting cells. The protein or peptide may be represented as such, as DNA (e.g. within a vector) or as RNA. The protein or peptide may be processed so as to produce a peptide partner for the HLA molecule. A presentation is also possible without further processing being required. This is the case in particular if peptides can bind to HLA molecules. Preference is given to administrative forms in which the total antigen is processed in vivo by a dendritic cell, since this may also produce helper T cell responses which are required for an effective immune response (Ossendorp et al., *Immunol Lett.* 74:75-79, 2000; Ossendorp et al., *J. Exp. Med.* 187:693-702, 1998).

The pharmaceutical compositions described according to the invention may also be employed as vaccines for immunization. The terms "immunization" or "vaccination" relate according to the invention to an increase or an activation of an immune reaction against an antigen. Animal models may be employed for testing an immunizing effect against cancer. It is possible, for example, for human cancer cells to be introduced into a mouse to create a tumor, and for one or more nucleic acids which code for proteins or peptides characteristic for cancer cells to be administered. The effect on the cancer cells (for example reduction in tumor size) can be measured as criterion for the efficacy of an immunization by the nucleic acid.

As part of the composition for immunization, preference is given to administering one or more antigens or stimulating fragments thereof together with one or more adjuvants to induce an immune response or increase an immune response. An adjuvant is a substance which is incorporated into the antigen or is administered together therewith and enhances the immune response. Adjuvants are able to enhance the immune response by providing an antigen reservoir (extracellularly or in macrophages), activating macrophages and/or stimulating certain lymphocytes. Adjuvants are known and include in a nonlimiting manner monophosphoryl-lipid-A (MPL, SmithKline Beecham), saponins such as QS21 (SmithKline Beecham), DQS21 (SmithKline Beecham; WO 96/33739), QS7, QS17, QS18 and QS-L1 (So et al., *Mol. Cells.* 7:178-186, 1997), incomplete Freund's adjuvant, complete Freund's adjuvant, vitamin E, montanide, alum, CpG oligonucleotides (cf. Kreig et al., *Nature* 374:546-9, 1995) and various water-in-oil emulsions which are prepared from biodegradable oils such as squalene and/or tocopherol. Preference is given to administering peptides in a mixture with DQS21/MPL. The ratio of DQS21 to MPL is typically about 1:10 to 10:1, preferably about 1:5 to 5:1 and in particular about 1:1. In a vaccine formulation for administration to humans, DQS21 and MPL are typically present in a range from about 1 µg to about 100 µg.

Other substances which stimulate an immune response in the patient may also be administered. For example, cytokines can be used for a vaccination because of their regulatory properties on lymphocytes. Such cytokines include, for example, interleukin-12 (IL-12) which has been shown to enhance the protective effects of vaccines (cf. *Science* 268: 1432-1434, 1995), GM-CSF and IL-18.

The invention also provides for administration of nucleic acids, proteins or peptides. Proteins and peptides may be administered in a manner known per se. In one embodiment, nucleic acids are administered by ex vivo methods, i.e. by removing cells from a patient, genetically modifying said cells in order to introduce a nucleic acid, and reintroducing the modified cells into the patient. This usually comprises introducing in vitro a functional copy of a gene into the cells of a patient and returning the genetically modified cells to the patient. The functional copy of the gene is under the functional control of regulatory elements which allow the gene to be expressed in the genetically modified cells. Transfection and transduction methods are known to the skilled worker. The invention also provides for administration of nucleic acids in vivo by using vectors such as viruses and targeted liposomes.

In a preferred embodiment, a viral vector for administering a nucleic acid is selected from the group consisting of adenoviruses, adeno-associated viruses, poxviruses, including vaccinia virus and attenuated poxviruses, Semliki forest virus, retroviruses, Sindbis virus and Ty virus-like particles. Particular preference is given to adenoviruses and retroviruses. The retroviruses are normally replication-deficient (i.e. they are unable to produce infectious particles).

Various methods may be employed in order to introduce nucleic acids into cells in vitro or in vivo according to the invention. Such methods include transfection of nucleic acid-calcium phosphate precipitates, transfection of nucleic acids associated with DEAE, transfection or infection with the above viruses carrying the nucleic acids of interest, liposome-mediated transfection and the like. In particular embodiments, guiding of the nucleic acid to particular cells is preferred. In such embodiments, a carrier employed for administering a nucleic acid to a cell (e.g. a retrovirus or a liposome) may have a bound targeting molecule. For example, a molecule such as an antibody which is specific to a surface membrane protein on the target cell, or a ligand for a receptor on the target cell, may be incorporated into the nucleic acid carrier or bound thereto. If administration of a nucleic acid by liposomes is desired, it is possible to incorporate proteins which bind to a surface membrane protein which is associated with endocytosis into the liposome formulation in order to make targeting and/or uptake possible. Such proteins include capsid proteins or fragments thereof, which are specific to a particular cell type, antibodies to proteins which are internalized, proteins which target an intracellular site, and the like.

The pharmaceutical compositions of the invention may be administered in pharmaceutically suitable preparations. Such preparations may usually comprise pharmaceutically suitable concentrations of salts, buffering substances, preservatives, carriers, supplementary immunity-enhancing substances such as adjuvants, CpG oligonucleotides, cytokines, chemokines, saponin, GM-CSF and/or RNA and, where appropriate, other therapeutic agents.

The therapeutic agents of the invention may be administered in any conventional way, including by injection or by infusion. The administration may be carried out, for example, orally, intravenously, intraperitoneally, intramuscularly, subcutaneously, or transdermally. Therapeutical administration of antibodies is preferably carried out by way of a lung aerosol. Antisense nucleic acids are preferably administered by slow intravenous administration.

The compositions of the invention are administered in effective amounts. An "effective amount" relates to the amount which, alone or together with further doses, achieves a desired response or a desired effect. In the case of treatment of a particular disease or of a particular condition, the desired response preferably relates to inhibition of the course of the disease. This includes slowing down the progression of the disease and in particular stopping or reversing said progression of the disease. The desired response on treatment of a disease or of a condition may also be that of delaying the onset or preventing the onset of said disease or condition.

An effective amount of a composition of the invention depends on the condition to be treated, the severity of the disease, the individual patient's parameters, including age, physiological condition, height and weight, the duration of the treatment, the nature of a concomitant therapy (if present), the specific administration route and similar factors.

The pharmaceutical compositions of the invention are preferably sterile and comprise an effective amount of the therapeutically active substance to generate the desired response or the desired effect.

The doses of the compositions of the invention which are administered may depend on various parameters such as the mode of administration, the patient's condition, the desired administration period, etc. In the case where a patient's response is inadequate with an initial dose, it is possible to employ higher doses (or effectively higher doses which are achieved by different, more localized administration route).

In general, doses of from 1 ng to 1 mg, preferably from 10 ng to 100 µg, of peptides and proteins are formulated and administered for a treatment or for generating or increasing an immune response. If it is desired to administer nucleic acids (DNA and RNA), doses of from 1 ng to 0.1 mg are formulated and administered.

The pharmaceutical compositions of the invention are generally administered in pharmaceutically suitable amounts and in pharmaceutically suitable compositions. The term "pharmaceutically suitable" relates to a nontoxic material which does not interact with the effect of the active ingredient of the pharmaceutical composition. Such preparations may usually comprise salts, buffering substances, preservatives, carriers and, where appropriate, other therapeutic agents. When used in medicine, the salts should be pharmaceutically suitable. Non-pharmaceutically suitable salts may, however, be used to prepare pharmaceutically suitable salts thereof and are encompassed by the invention. Such pharmacologically and pharmaceutically suitable salts include in a non-limiting manner those prepared from the following acids: hydrochloric, hydrobromic, sulfuric, nitric, phosphoric, maleic, acetic, salicylic, citric, formic, malonic, succinic acids and the like. Pharmaceutically suitable salts may also be prepared as alkali metal or alkaline earth metal salts such as sodium, potassium or calcium salts.

A pharmaceutical composition of the invention may comprise a pharmaceutically suitable carrier. The term "pharmaceutically suitable carrier" relates according to the invention to one or more compatible solid or liquid fillers, diluents or capsule substances which are suitable for administration to a human. The term "carrier" relates to an organic or inorganic component, natural or synthetic in nature, in which the active component is combined in order to facilitate application. The components of the pharmaceutical composition of the invention are usually such that no interaction which substantially impairs the desired pharmaceutical efficacy occurs.

The pharmaceutical compositions of the invention may include suitable buffering substances such as acetic acid in a salt, citric acid in a salt, boric acid in a salt and phosphoric acid in a salt.

The pharmaceutical compositions may also include, where appropriate, suitable preservatives such as benzalkonium chloride, chlorobutanol, parabens and thimerosal.

The pharmaceutical compositions are usually presented in a unit dose form and can be produced in a manner known per se. Pharmaceutical compositions of the invention may be, for example, in the form of capsules, tablets, lozenges, suspensions, syrups, elixirs or as emulsion.

Compositions suitable for parenteral administration usually comprise a sterile aqueous or nonaqueous preparation of the agent, which is preferably isotonic with the recipient's blood. Examples of suitable carriers and solvents are Ringer's solution and isotonic sodium chloride solution. In addition, sterile, fixed oils are usually employed as dissolving or suspending medium.

The present invention is described in detail by the following figures and examples which serve exclusively for illustration purposes and are not to be understood as limiting. Further embodiments which are likewise encompassed by the invention are accessible to the skilled worker on the basis of the description and the examples.

FIGURES

FIG. 1. Northern blot analysis using an EDI-3-specific probe

RNA was obtained from testis, skeletal muscle, liver, lung, spleen, brain and heart (lanes 1-8). Expression of EDI-3 transcript was found in testis (lane 1), skeletal muscle (lane 3) and heart (lane 8).

Figure 2:
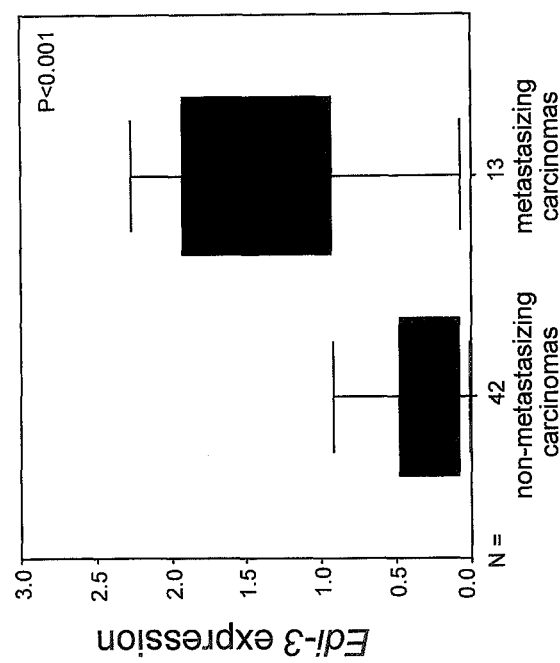

FIG. 2. Expression of EDI-3 in primary endometrial carcinomas

Expression was found to be elevated by a factor of 6.4 in metastasizing tumors in comparison with non-metastasizing tumors (p≤0.001; Mann-Whitney test, double-sided). Only patients observed over a period of at least 5 years were included. However, a difference regarding expression of EDI-3 is also obtained when all 57 patients, also including those observed over periods shorter than 5 years are included (p<0.001, data not shown). The horizontal line in the center of a box indicates the median of the sample. The edges of a box indicate the 25th and 75th percentiles. The whiskers indicate the range of values within 1.5 box lengths.

Figure 3:
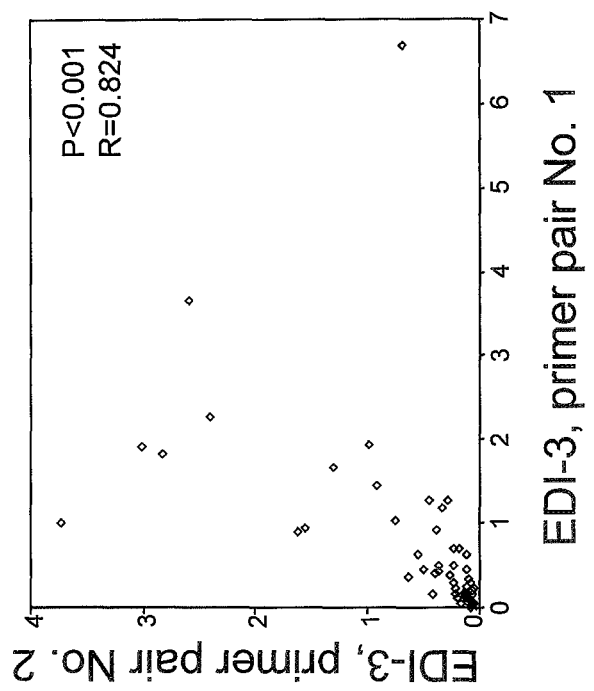

FIG. 3. Confirmation experiment using a second primer pair for quantifying EDI-3 mRNA expression Primer pair No. 1 amplifies a fragment between by positions 2872 and 3172, while primer pair No. 2 results in amplification between by positions 3161 and 3362. Quantitative PCR produced a correlation with p<0.001 and R=0.824.

Figure 4:
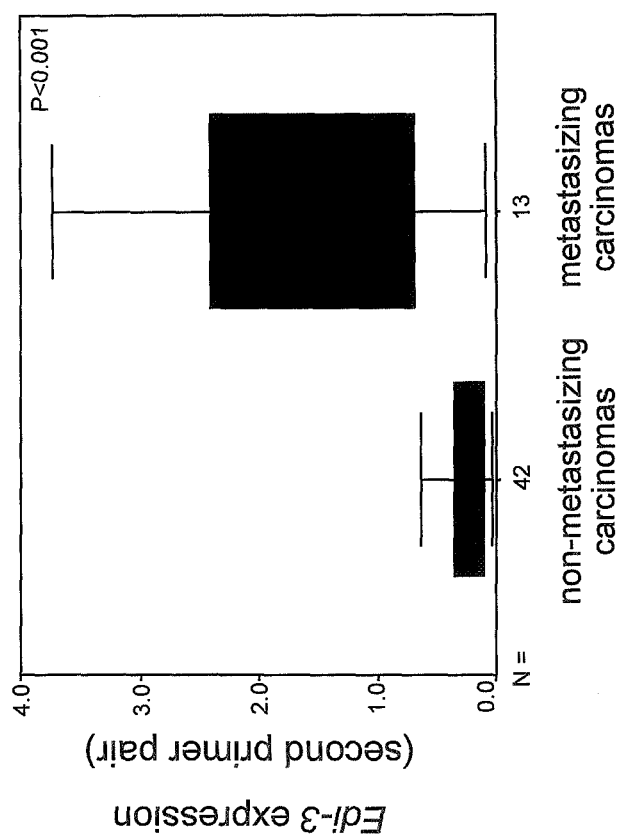

FIG. 4. Confirmation experiment using a second primer pair for quantifying EDI-3 mRNA expression Similarly to the results obtained with the first primer pair, higher expression of EDI-3 was found in metastasizing tumors in comparison with non-metastasizing tumors (p<0.001, Mann-Whitney test, double sided). Only patients observed over a period of at least five years were taken into account. The horizontal line in the center of a box indicates the median of the sample. The edges of a box mark the 25th and 75th percentiles. The whiskers indicate the range of values within 1.5 box lengths.

Figure 5:
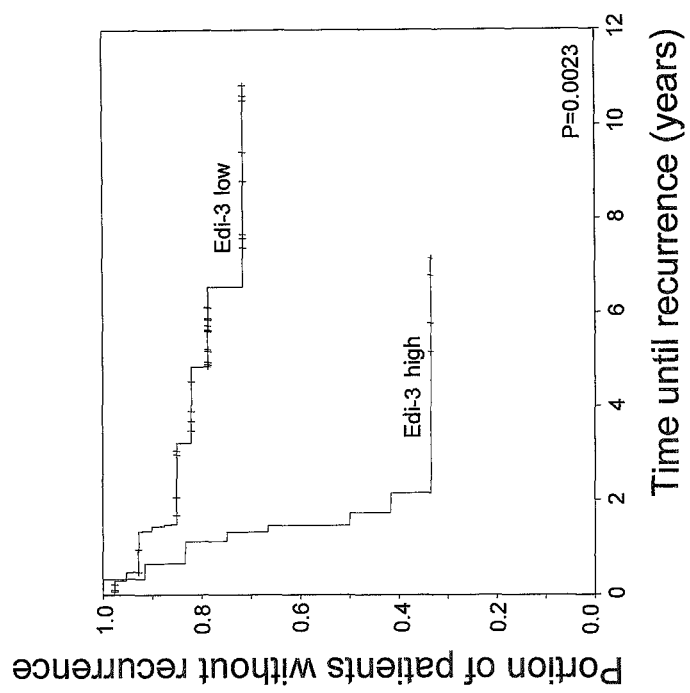

FIG. 5. Kaplan-Meier analysis of the association between expression of the EDI-3 transcript and the time span until a recurrence upon resection of endometrial cancer tissue EDI-3 expression was dichotomized using the 75% percentile (p=0.0023, logrank test).

Figure 6:
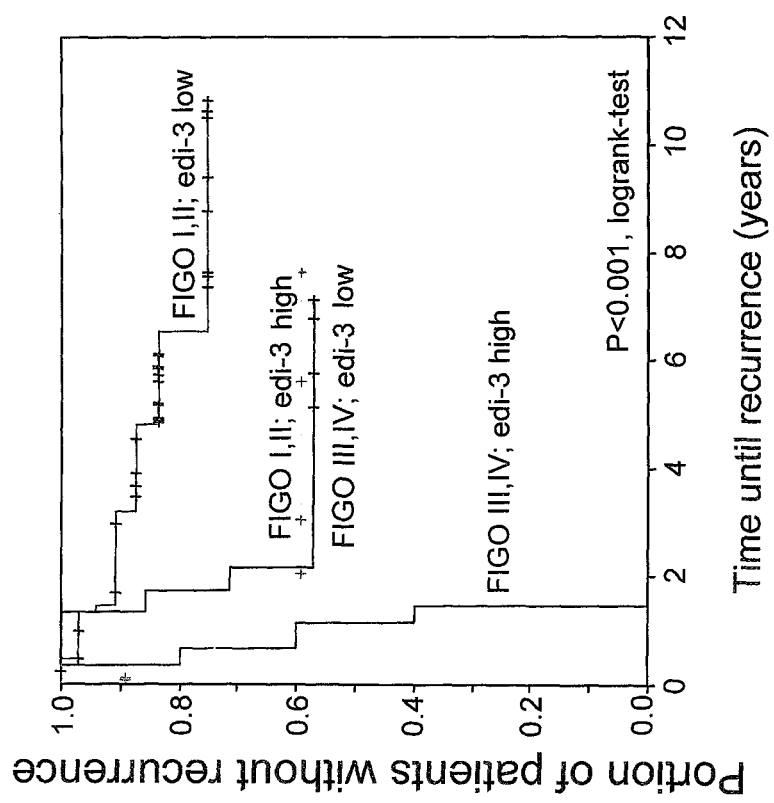

FIG. 6. Kaplan-Meier analysis of the association between expression of the EDI-3 transcript and the time span until a recurrence as a function of the FIGO stage EDI-3 expression was dichotomized using the 75% percentile.

Figure 7:
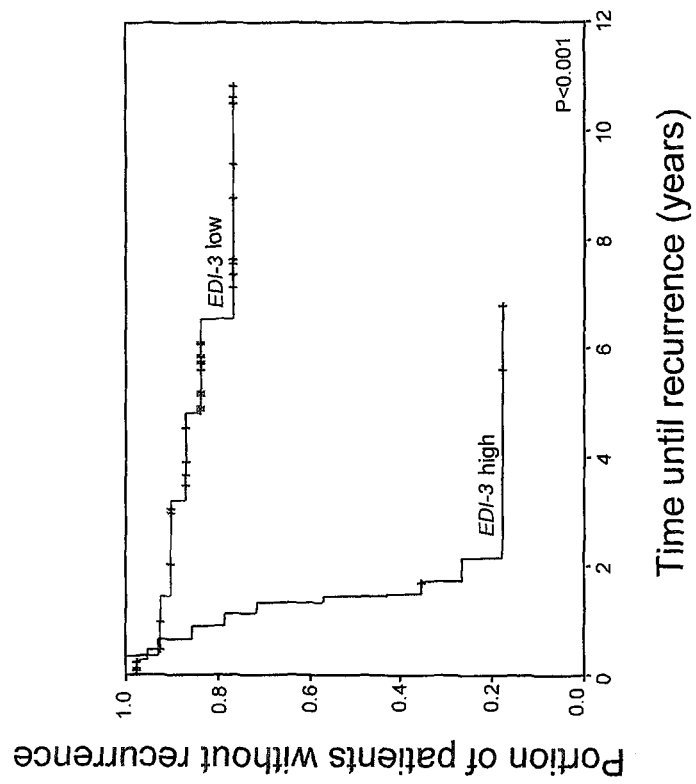

FIG. 7. Confirmation experiment using a second primer pair for quantifying EDI-3 mRNA expression Similarly to the results obtained with the first primer pair, the time span until the occurrence of a recurrence was longer for patients with low EDI-3 expression in comparison with patients with high EDI-3 expression upon resection of endometrial cancer tissue. EDI-3 was dichotomized at the 75% percentile (p<0.001, logrank test).

EXAMPLES

Example 1

Patients and Tissue Samples

Between 1985 and 2000, 269 patients with histologically confirmed cancer of the endometrium were treated in the department of obstetrics and gynecology at the University Hospital in Mainz, Germany.

High-quality RNA was obtainable from only 63 of these patients for three reasons: (i) parts of the tumor samples used for RNA analysis were additionally examined histologically. If the fraction of tumor cells was less than 95%, the sample was not included in the present study. (ii) It was not possible to freeze any tissue from some patients with small tumors. (iii) The quality of some RNA samples was not sufficient based on the ratio of 28S and 18S bands, or expression of the constitutive huPO (human phosphoprotein) gene was too low (Mohrmann G. et al., Int. J. Cancer, in press, 2005). Based on information from clinical records, including surgery reports and pathological reports, a database was generated. The histological tumor type and grade, the weight, height and age of the patients, diabetes mellitus, the FIGO stage, the type of a surgery and the pathological TNM classification were included. The FIGO stage followed the surgical stage determination system for endometrial carcinomas from 1988 (Creasman W T, Gynecol Oncol 1989; 35: 125-7). The body mass index (BMI) was calculated using the formula BMI= [weight/(height)$^2$]. The recurrence-free time was calculated as the difference between the date of a surgical treatment and the date of a documentation of a recurrence. Recurrences developed due to new tumor growth in paraaortic lymph nodes, pelvis, bones, lung, liver and vagina. All histological samples were evaluated by an experienced pathologist. All tumors were classified according to the WHO/ISGPY classification (Scully R E et al., International Classification and Histologic Typing of Female Genital Tract Tumours. Springer: New York, 1994). The tumor grade was determined according to Kurman et al. (Kurman R J et al., In: Kurman RJ, ed. Blaustein's Pathology of the Female Genital Tract, 4th edn. Springer: New York, 1994, 439-86), taking into account structural features and core features. The depth of invasion was classified according to Sevin and Angioli (Sevin B-U, Angioli R. Uterine Corpus: Multimodality Therapy in Gynecologic Oncology. Thieme: New York, 1996) as a function of infiltration of the inner, center and outer third of the myometrium. For RNA isolation, only histologically controlled tumor samples containing at least 95% tumor cells without non-neoplastic endometrium or myometrium were included in the study. A standard surgical procedure was abdominal hysterectomy and bilateral salpingo ovariectomy. Lymph nodes were dissected in cases in which intrasurgical frozen sections showed infiltration of the outer third of the myometrium and also in cases with cervical involvement, depending on factors of general morbidity of the patient.

Among the 63 patients with available RNA of high quality, three pairs of patients with identical FIGO stage, grade, histopathological tumor type, type of surgery, menopausal state, depth of invasion into the myometrium, and a similar body mass index were selected. These pairs comprised in each case one patient who developed metastases within five years after surgery and another patient who was not found to have any metastases within the observation period of at least five years. The six connected patients ("screening set of tumors") were used for identifying differentially expressed genes.

The remaining 57 patients served as "validation set" and comprised 13 patients who developed metastases later, while the other patients remained tumor-free. The "validation set" was used in order to address two questions with regard to candidate genes which had been identified in the "screening set" of tumors: (i) did primary tumors of patients who later developed metastases show higher expression of a candidate gene than patients without metastases? (ii) were candidate genes identified in the "screening set of tumors", which were associated with the period until a recurrence in a multivariate analysis? The patients' characteristics are summarized in table 1.

TABLE 1

Properties of the "validation set" of patients with primary endometrial carcinomas
Primary endometrial carcinomas (n = 57)

|  | Number evaluated (n = 57) | % | Not analyzable |
|---|---|---|---|
| FIGO stage |  |  | 1 |
| Stage I | 35 | 62.5 |  |
| Stage II | 7 | 12.5 |  |
| Stage III | 11 | 19.6 |  |
| Stage IV | 3 | 5.4 |  |
| Histological grade |  |  | 2 |
| Grade I | 18 | 32.7 |  |
| Grade II | 23 | 41.8 |  |
| Grade III | 14 | 25.5 |  |
| Depth of invasion[1] |  |  | 0 |
| low | 21 | 36.8 |  |
| high | 36 | 63.2 |  |
| Metastasis[2] |  |  | 2 |
| No | 42 | 76.4 |  |
| Yes | 13 | 23.6 |  |

TABLE 1-continued

Properties of the "validation set" of patients with
primary endometrial carcinomas
Primary endometrial carcinomas (n = 57)

| | Number evaluated (n = 57) | % | Not analyzable |
|---|---|---|---|
| Menopausal status | | | 0 |
| pre | 6 | 10.5 | |
| post | 51 | 89.5 | |
| Age at surgery (years, average ± standard deviation) | 68.5 ± 11.5 | | |
| Height (cm, average ± standard deviation) | 163 ± 5.2 | | |
| Weight (kg, average ± standard deviation) | 79.5 ± 16.9 | | |

[1]Depth of invasion was classified as low (infiltration of no more than the inner third of the myometrium) and high (infiltration of the center and outer thirds of the myometrium).
[2]Metastasis: After the primary tumor had been removed by standard surgery (abdominal hysterectomy and bilateral salpingo ovariectomy), two classes were distinguished: (i) "no metastasis", if the patient remained tumor-free, (ii) "metastasis", if renewed tumor growth was found at any of the following sites: paraaortic lymph nodes, pelvis, bones, lung, liver or vagina.

Example 2

Differential Display

RNA from frozen tissue was isolated using a commercially available kit (MidiKit, Qiagen, Hilden, Germany). The quality of the isolated RNA was evaluated by way of the ratio of the 28S and 18S bands on a 1% agarose gel and by way of expression of the constitutive huPO gene, as described earlier (Mohrmann G et al., Int. J. Cancer, in press, 2005). The concentrations of the isolated RNA were determined spectrophotometrically. Reverse transcription was carried out using the Delta™ Differential Display Kit (Clontech, Heidelberg, Germany). Amplification was obtained using the P and T primers depicted below (Arbitrary Primer, Clontech, Heidelberg, Germany):

```
P primers
                                        (SEQ ID NO: 9)
P1:  5'-ATTAACCCTCACTAAATGCTGGGGA-3'

(SEQ ID NO: 10)
P2:  5'-ATTAACCCTCACTAAATCGGTCATAG-3'

(SEQ ID NO: 11)
P3:  5'-ATTAACCCTCACTAAATGCTGGTGG-3'

(SEQ ID NO: 12)
P4:  5'-ATTAACCCTCACTAAATGCTGGTAG-3'

(SEQ ID NO: 13)
P5:  5'-ATTAACCCTCACTAAAGATCTGACTG-3'

(SEQ ID NO: 14)
P6:  5'-ATTAACCCTCACTAAATGCTGGGTG-3'

(SEQ ID NO: 15)
P7:  5'-ATTAACCCTCACTAAATGCTGTATG-3'

(SEQ ID NO: 16)
P8:  5'-ATTAACCCTCACTAAATGGAGCTGG-3'

(SEQ ID NO: 17)
P9:  5'-ATTAACCCTCACTAAATGTGGCAGG-3'

(SEQ ID NO: 18)
P10: 5'-ATTAACCCTCACTAAAGCACCGTCC-3'

T primers
                                        (SEQ ID NO: 19)
T1:  5'-CATTATGCTGAGTGATATCTTTTTTTTTAA-3'

(SEQ ID NO: 20)
T2:  5'-CATTATGCTGAGTGATATCTTTTTTTTTAC-3'

(SEQ ID NO: 21)
T3:  5'-CATTATGCTGAGTGATATCTTTTTTTTTAG-3'

(SEQ ID NO: 22)
T4:  5'-CATTATGCTGAGTGATATCTTTTTTTTTCA-3'

(SEQ ID NO: 23)
T5:  5'-CATTATGCTGAGTGATATCTTTTTTTTTCC-3'

(SEQ ID NO: 24)
T6:  5'-CATTATGCTGAGTGATATCTTTTTTTTTCG-3'

(SEQ ID NO: 25)
T7:  5'-CATTATGCTGAGTGATATCTTTTTTTTTGA-3'

(SEQ ID NO: 26)
T8:  5'-CATTATGCTGAGTGATATCTTTTTTTTTGC-3'

(SEQ ID NO: 27)
T9:  5'-CATTATGCTGAGTGATATCTTTTTTTTTGG-3'
```

The products of the first amplification were fractionated on 8% strength denaturing polyacrylamide gels and visualized by silver staining using the Rapid-Silver Stain Kit (ICN Biomedicals, Ohio, USA). Bands which were visible in samples of patients with metastases but which were absent in samples of patients with non-metastasizing tumors were excised, and the DNA was purified using the QiaExIIKit (Qiagen, Hilden, Germany). In order to prepare enough DNA for sequencing, the purified product was amplified again with the aid of the same primers used for identification. After purification by means of QIAquick columns (Qiagen, Hilden, Germany), the DNA sequence was determined by cyclic sequencing.

A differential display study of the "screening set of tumors" resulted in the identification of three transcripts, namely EDI-1, EDI-2 and EDI-3, which were present in tumors forming metastases, but were not expressed in non-metastasizing endometrial carcinomas.

EDI-1 was found by means of the Clontech primers P 3 and T 3 and was 260 bp in length in the polyacrylamide gel. After reamplification, purification and sequencing with the aid of the P 3 primer, the nucleic acid sequence depicted in SEQ ID NO: 1 was obtained.

EDI-2 was found by means of the Clontech primers P 2 and T 5 and was 190 bp in length in the polyacrylamide gel. After reamplification, purification and sequencing with the aid of the Clontech P 2 primer, the nucleic acid sequence depicted in SEQ ID NO: 2 was obtained.

EDI-3 was obtained by means of the Clontech primers P 3 and T 3 and was 270 bp in length in the polyacrylamide gel. After reamplification, purification and sequencing with the aid of the Clontech P 3 primer, the nucleic acid sequence depicted in SEQ ID NO: 3 was obtained.

The EDI-3 nucleic acid fragment sequenced has homology to a functionally not yet characterized transcript of 5444 bp (accession number AL109935.39.1.178601, SEQ ID NO: 7) containing a predicted open reading frame of 2016 bp. According to database information, the corresponding gene consists of 20 exons and is located on the short arm of chromosome 20 in the p13 band. Northern blot analysis confirmed the expected transcript size (FIG. 1).

Example 3

Quantitative RT-PCR

TaqMan analysis was carried out as described recently (Mohrmann G et al., Int. J. Cancer, in press, 2005). Briefly, total RNA was isolated from tumor tissue using the RNeasy Mini Kit (Qiagen, Hilden, Germany) and quantified by measuring the optical density at 260 nm. Two µg of total RNA were used for a cDNA synthesis mixture containing 2.5 µl of MultiScribe reverse transcriptase (50 U/µl, Applied Biosystems), 10 µl of RT buffer, 22 µl of 25 mM $MgCl_2$, 20 µl of dNTP mix (Applied Biosystems), 2 µl of RNase inhibitor (20 U/µl, Applied Biosystems), 5 µl of random hexamers (50 µM, Applied Biosystems) in a total volume of 100 µl. The mixture was incubated at 25° C. for 2 minutes, at 48° C. for 30 minutes, and the enzyme was inactivated at 95° C. for 5 minutes. All cDNAs were diluted by adding 150 µl of DEPC-treated water and stored at −20° C. A quantitative PCR analysis made use of the Taq-Man™PCR technology (Gene Amp 5700 sequence detection system, ABI, Weiterstadt, Germany). A PCR was carried out in a volume of 25 µl with 12.5 µl of SYBR GREEN PCR master mix (including enzyme buffer, fluorescent dye and nucleotides, Applied Biosystems), 5 µM of each primer (2.5 µl, 10 mM), 2.5 µl of DEPC-treated water and 5 µl of cDNA template. Two primer pairs were used for EDI-3 analysis: (i) 5'-TTTCA AAATG CTGCA GGGTA AT-3' (SEQ ID NO: 28) and 5'-ACCCA CAAAG CAACA GTGTG TA-3' (SEQ ID NO: 29), (ii) 5'-CACAA TCTGC TTCTA ATCCA AGAA-3' (SEQ ID NO: 30) and 5'-TGCTT TGTGG GTTTG TTTTG TA-3' (SEQ ID NO: 31). The PCR comprised preincubation at 50° C. for 2 minutes, followed by denaturation at 95° C. for 10 minutes. 40 cycles were carried out, including denaturation at 95° C. for 15 seconds, hybridization at 60° C. for 60 seconds and elongation at 72° C. for 30 seconds. The reaction was followed by the dissociation protocol, whereby the range between 60 and 94° C. was studied. Emission ranges of the fluorescent dye were measured in real time during the PCR, and relative mRNA quantification values were obtained from the threshold cycle number from which the increase in the signal associated with exponential growth of PCR product was detectable. The sequence detection system software, version 1.6 (ABI, Weiterstadt, Germany) was used. Quantification was normalized using the constitutive huPO (human phosphoprotein) gene according to Vlachtsis et al. (Vlachtsis K et al., Oncol Rep. 9: 1133-8, 2002). A negative control without reverse transcriptase was included in all PCR analyses.

Using the "validation set of carcinomas", it was investigated whether it was possible to confirm the difference regarding EDI-3 expression, found in the "screening set of tumors". A quantitative RT-PCR indicated increased EDI-3 expression by a factor of 6.4 in metastasizing endometrial carcinomas in comparison with non-metastasizing endometrial carcinomas (p<0.001, FIG. 2). Similar results were obtained in an independent study of the same RNA species using a second primer pair (FIGS. 3 and 4).

Example 4

Expression of EDI-3 Indicates Recurrence-Free Survival

If EDI-3 expression is associated with a formation of metastases, EDI-3 could be assumed to be an indicator for the absence of a recurrence. Expression of EDI-3 (dichotomized at the 75% percentile) was indeed associated with a recurrence-free survival (FIG. 5). The average time span until a recurrence was 1.47 years in the case of patients expressing large amounts of EDI-3. In contrast, 79% of patients with low EDI-3 expression were tumor-free 5 years after surgery (p=0.0023). Using the proportional hazards model, EDI-3 was significant in a univariate analysis (RR=4.3, P=0.002), and in a multivariate step-up regression analysis with the FIGO stage (I, II versus III, IV), an age of over 70 years, diabetes mellitus (y/n), grading (1, 2 versus 3) and the depth of invasion into the myometrium (0-2 mm versus 3+mm) as covariates (RR=3.6, P=0.012). Only EDI-3 expression and the FIGO stage were prognostic in a multivariate analysis (table 2).

TABLE 2

Association of EDI-3 expression with tumor-free survival in 57 patients with primary cancer of the endometrium ("validation set of tumors"), using the univariate and multivariate proportional hazards model (Cox analysis)

| Factor | Relative risk | 95% confidence interval | p value |
|---|---|---|---|
| Univariate analysis | | | |
| EDI-3 mRNA | 4.3 | 1.7-11.0 | 0.002 |
| Multivariate analysis | | | |
| Adjusted to FIGO stage (I, II vs. III, IV), grading (1, 2 vs. 3), depth of invasion (0-2 mm vs 3+ mm), age (under versus over 70 years) and diabetes mellitus | | | |
| EDI-3 mRNA | 3.6 | 1.3-9.7 | 0.012 |
| FIGO stage (stage I, II vs III, IV) | 5.1 | 1.8-14.0 | 0.002 |

An adjustment with respect to the FIGO stage could be problematic due to a possible violation of the proportional hazards assumption on which the Cox model is based, and the small sample size. However, the effect of EDI-3 remains significant, if the FIGO stage is included as a factor in the Cox model (p=0.012), as well as if the FIGO stage is used for stratification, assuming different hazard functions for a restricted (FIGO I, II) and advanced (FIGO III, IV) disease (p<0.001, FIG. 6). In order to test reproducibility of the quantitative RT-PCR, the same mRNA species were additionally studied using a second primer pair directed to a region of the EDI-3 transcript located further downstream. Data obtained with the second primer pair corresponded to those of the first primer pair (p<0.001, R=0.824) and confirmed a relationship between EDI-3 expression and a recurrence-free survival (table 3, FIG. 7).

TABLE 3

Confirmation experiment using a second primer pair for quantifying EDI-3 mRNA expression. Similarly to the results obtained with the first primer pair, expression of the EDI-3 transcript was associated with tumor-free survival in 57 patients with primary cancer of the endometrium ("validation set of tumors"), using the univariate and multivariate proportional hazards model (Cox analysis)

| Factor | Relative risk | 95% confidence interval | p value |
|---|---|---|---|
| Univariate analysis | | | |
| EDI-3 mRNA | 7.9 | 3.0-21.3 | <0.001 |
| Multivariate analysis | | | |
| Adjusted to FIGO stage (I, II vs. III, IV), grading (1, 2 vs. 3), depth of invasion (0-2 mm vs 3+ mm), age (under versus over 70 years) and diabetes mellitus | | | |
| EDI-3 mRNA | 7.3 | 2.7-19.9 | <0.001 |

The invention claimed is:

1. A method of diagnosing metastasizing endometrial carcinoma in a human patient, comprising:

analyzing an endometrial carcinoma tissue sample from the patient for expression of EDI-3; wherein the expression level of EDI-3 is analyzed by:

detecting and/or determining the expression of an RNA transcript of a nucleic acid encoding EDI-3 (SEQ ID NO: 7) or a fragment thereof by isolating total RNA from the tissue sample and performing quantitative PCR on the total RNA with primers suitable for amplification of a cDNA transcript of greater than 200 consecutive nucleotides of SEQ ID NO: 7 from the region between nucleotides 2872 to 3362 thereof;

and diagnosing that the endometrial carcinoma of the patient is likely to metastasize when the level of expression EDI-3 in the tissue sample from the patient is 6.4 times or greater than the average level of expression of EDI-3 in human endometrial carcinoma tissue from patients with non-metastasizing endometrial carcinoma.

2. The method of claim 1 wherein the quantitative PCR utilizes at least one primer selected from the group consisting of SEQ ID NO: 28, SEQ ID NO: 29, SEQ ID NO: 30, and SEQ ID NO: 31 in the amplification of the cDNA.

* * * * *

SEQUENCE LISTING

<160> NUMBER OF SEQ ID NOS: 31

<210> SEQ ID NO 1
<211> LENGTH: 162
<212> TYPE: DNA
<213> ORGANISM: Homo sapiens
<220> FEATURE:
<221> NAME/KEY: misc_feature
<222> LOCATION: (5)..(5)
<223> OTHER INFORMATION: unsure
<220> FEATURE:
<221> NAME/KEY: misc_feature
<222> LOCATION: (8)..(8)
<223> OTHER INFORMATION: unsure
<220> FEATURE:
<221> NAME/KEY: misc_feature
<222> LOCATION: (17)..(17)
<223> OTHER INFORMATION: unsure
<220> FEATURE:
<221> NAME/KEY: misc_feature
<222> LOCATION: (20)..(20)
<223> OTHER INFORMATION: unsure
<220> FEATURE:
<221> NAME/KEY: misc_feature
<222> LOCATION: (25)..(25)
<223> OTHER INFORMATION: unsure
<220> FEATURE:
<221> NAME/KEY: misc_feature
<222> LOCATION: (26)..(26)
<223> OTHER INFORMATION: unsure
<220> FEATURE:
<221> NAME/KEY: misc_feature
<222> LOCATION: (29)..(29)
<223> OTHER INFORMATION: unsure
<220> FEATURE:
<221> NAME/KEY: misc_feature
<222> LOCATION: (36)..(36)
<223> OTHER INFORMATION: unsure
<220> FEATURE:
<221> NAME/KEY: misc_feature
<222> LOCATION: (44)..(44)
<223> OTHER INFORMATION: unsure
<220> FEATURE:
<221> NAME/KEY: misc_feature
<222> LOCATION: (46)..(46)
<223> OTHER INFORMATION: unsure
<220> FEATURE:
<221> NAME/KEY: misc_feature
<222> LOCATION: (50)..(50)
<223> OTHER INFORMATION: unsure

<400> SEQUENCE: 1
ttaanccnct ttttatnccn ttaannaana aaatantttc agtncntcan gagctgggaa      60
actgtatcca ggatgtactc aaacacatgt ttacatattg tctaccgagc ttcaggctga    120
attagtaata gcttactgcc aaaaggataa tatttatgac ca                       162

<210> SEQ ID NO 2
<211> LENGTH: 51
<212> TYPE: DNA
<213> ORGANISM: Homo sapiens
<220> FEATURE:
<221> NAME/KEY: misc_feature
<222> LOCATION: (30)..(30)
<223> OTHER INFORMATION: unsure

<400> SEQUENCE: 2
cccttctccc tgcactcaat aaaccctcan taaatattct cattgtcaat c              51

<210> SEQ ID NO 3
<211> LENGTH: 156
<212> TYPE: DNA
<213> ORGANISM: Homo sapiens

```
<220> FEATURE:
<221> NAME/KEY: misc_feature
<222> LOCATION: (5)..(5)
<223> OTHER INFORMATION: unsure

<400> SEQUENCE: 3
tgcanactta gtagaataga tcacaacata caaattcaat tcagtgcatg ctttaggtgt      60
taagcatgag attgtacatg tttactgtta ggtccttgca tctgtggtgc taggtgagta     120
tgagaagatg tcaaggactg gacgtatttt tgttgc                               156

<210> SEQ ID NO 4
<211> LENGTH: 126
<212> TYPE: DNA
<213> ORGANISM: Homo sapiens
<220> FEATURE:
<221> NAME/KEY: misc_feature
<222> LOCATION: (8)..(8)
<223> OTHER INFORMATION: unsure
<220> FEATURE:
<221> NAME/KEY: misc_feature
<222> LOCATION: (10)..(10)
<223> OTHER INFORMATION: unsure
<220> FEATURE:
<221> NAME/KEY: misc_feature
<222> LOCATION: (14)..(14)
<223> OTHER INFORMATION: unsure

<400> SEQUENCE: 4
tttcagtncn tcangagctg ggaaactgta tccaggatgt actcaaacac atgtttacat      60
attgtctacc gagcttcagg ctgaattagt aatagcttac tgccaaaagg ataatattta    120
tgacca                                                               126

<210> SEQ ID NO 5
<211> LENGTH: 70
<212> TYPE: DNA
<213> ORGANISM: Homo sapiens

<400> SEQUENCE: 5
acatattgtc taccgagctt caggctgaat tagtaatagc ttactgccaa aaggataata     60
tttatgacca                                                            70

<210> SEQ ID NO 6
<211> LENGTH: 145
<212> TYPE: DNA
<213> ORGANISM: Homo sapiens

<400> SEQUENCE: 6
acttagtaga atagatcaca acatacaaat tcaattcagt gcatgcttta ggtgttaagc     60
atgagattgt acatgtttac tgttaggtcc ttgcatctgt ggtgctaggt gagtatgaga    120
agatgtcaag gactggacgt atttt                                          145

<210> SEQ ID NO 7
<211> LENGTH: 5444
<212> TYPE: DNA
<213> ORGANISM: Homo sapiens
<220> FEATURE:
<221> NAME/KEY: CDS
<222> LOCATION: (206)..(2224)
<223> OTHER INFORMATION:

<400> SEQUENCE: 7
ctggagcagc tgaaaccggt ttgagcgtgg ctgcttcctg ccgctcgacg ccgcggcagg      60
```

```
ccgcctgggg ggagcgctgg cgaggcacgg acggcgggcg cccggtacct ctgcccgcgg      120
tcctcgctct cgggcgggc ggcggcgacg cggacctgcg gactagcgaa cccggagcac       180
gacatcataa aataaatcca tcaga atg aca cct tct cag gtt gcc ttt gaa        232
                            Met Thr Pro Ser Gln Val Ala Phe Glu
                            1               5 ata aga gga act ctt tta cca gga gaa gtt ttt gcg ata tgt gga agc        280
Ile Arg Gly Thr Leu Leu Pro Gly Glu Val Phe Ala Ile Cys Gly Ser
10              15                  20                  25 tgt gat gct ttg gga aac tgg aat cct caa aat gct gtg gct ctt ctt        328
Cys Asp Ala Leu Gly Asn Trp Asn Pro Gln Asn Ala Val Ala Leu Leu
            30                  35                  40 cca gag aat gac aca ggt gaa agc atg cta tgg aaa gca acc att gta        376
Pro Glu Asn Asp Thr Gly Glu Ser Met Leu Trp Lys Ala Thr Ile Val
                45                  50                  55 ctc agt aga gga gta tca gtt cag tat cgc tac ttc aaa ggg tac ttt        424
Leu Ser Arg Gly Val Ser Val Gln Tyr Arg Tyr Phe Lys Gly Tyr Phe
            60                  65                  70 tta gaa cca aag act atc ggt ggt cca tgt caa gtg ata gtt cac aag        472
Leu Glu Pro Lys Thr Ile Gly Gly Pro Cys Gln Val Ile Val His Lys
75                  80                  85 tgg gag act cat cta caa cca cga tca ata acc cct tta gaa agc gaa        520
Trp Glu Thr His Leu Gln Pro Arg Ser Ile Thr Pro Leu Glu Ser Glu
90                  95                  100                 105 att att att gac gat gga caa ttt gga atc cac aat ggt gtt gaa act        568
Ile Ile Ile Asp Asp Gly Gln Phe Gly Ile His Asn Gly Val Glu Thr
                110                 115                 120 ctg gat tct gga tgg ctg aca tgt cag act gaa ata aga tta cgt ttg        616
Leu Asp Ser Gly Trp Leu Thr Cys Gln Thr Glu Ile Arg Leu Arg Leu
            125                 130                 135 cat tat tct gaa aaa cct cct gtg tca ata acc aag aaa aaa tta aaa        664
His Tyr Ser Glu Lys Pro Pro Val Ser Ile Thr Lys Lys Lys Leu Lys
        140                 145                 150 aaa tct aga ttt agg gtg aag ctg aca cta gaa ggc ctg gag gaa gat        712
Lys Ser Arg Phe Arg Val Lys Leu Thr Leu Glu Gly Leu Glu Glu Asp
    155                 160                 165 gac gat gat agg gta tct ccc act gta ctc cac aaa atg tcc aat agc        760
Asp Asp Asp Arg Val Ser Pro Thr Val Leu His Lys Met Ser Asn Ser
170                 175                 180                 185 ttg gag ata tcc tta ata agc gac aat gag ttc aag tgc agg cat tca        808
Leu Glu Ile Ser Leu Ile Ser Asp Asn Glu Phe Lys Cys Arg His Ser
                190                 195                 200 cag ccg gag tgt ggt tat ggc ttg cag cct gat cgt tgg aca gag tac        856
Gln Pro Glu Cys Gly Tyr Gly Leu Gln Pro Asp Arg Trp Thr Glu Tyr
            205                 210                 215 agc ata cag acg atg gaa cca gat aac ctg gaa cta atc ttt gat ttt        904
Ser Ile Gln Thr Met Glu Pro Asp Asn Leu Glu Leu Ile Phe Asp Phe
        220                 225                 230 ttc gaa gaa gat ctc agt gag cac gta gtt cag ggt gat gcc ctt cct        952
Phe Glu Glu Asp Leu Ser Glu His Val Val Gln Gly Asp Ala Leu Pro
    235                 240                 245 gga cat gtg ggt aca gct tgt ctc tta tca tcc acc att gct gag agt        1000
Gly His Val Gly Thr Ala Cys Leu Leu Ser Ser Thr Ile Ala Glu Ser
250                 255                 260                 265 gga aag agt gct gga att ctt act ctt ccc atc atg agc aga aat tcc        1048
Gly Lys Ser Ala Gly Ile Leu Thr Leu Pro Ile Met Ser Arg Asn Ser
                270                 275                 280 cgg aaa aca ata ggc aaa gtg aga gtt gac tat ata att att aag cca        1096
Arg Lys Thr Ile Gly Lys Val Arg Val Asp Tyr Ile Ile Ile Lys Pro
            285                 290                 295
```

```
tta cca gga tac agt tgt gac atg aaa tct tca ttt tcc aag tat tgg   1144
Leu Pro Gly Tyr Ser Cys Asp Met Lys Ser Ser Phe Ser Lys Tyr Trp
        300                 305                 310 aag cca aga ata cca ttg gat gtt ggc cat cga ggt gca gga aac tct   1192
Lys Pro Arg Ile Pro Leu Asp Val Gly His Arg Gly Ala Gly Asn Ser
315                 320                 325 aca aca act gcc cag ctg gct aaa gtt caa gaa aat act att gct tct   1240
Thr Thr Thr Ala Gln Leu Ala Lys Val Gln Glu Asn Thr Ile Ala Ser
330                 335                 340                 345 tta aga aat gct gct agt cat ggt gca gcc ttt gta gaa ttt gac gta   1288
Leu Arg Asn Ala Ala Ser His Gly Ala Ala Phe Val Glu Phe Asp Val
            350                 355                 360 cac ctt tca aag gac ttt gtg ccc gtg gta tat cat gat ctt acc tgt   1336
His Leu Ser Lys Asp Phe Val Pro Val Val Tyr His Asp Leu Thr Cys
                365                 370                 375 tgt ttg act atg aaa aag aaa ttt gat gct gat cca gtt gaa tta ttt   1384
Cys Leu Thr Met Lys Lys Lys Phe Asp Ala Asp Pro Val Glu Leu Phe
        380                 385                 390 gaa att cca gta aaa gaa tta aca ttt gac caa ctc cag ttg tta aag   1432
Glu Ile Pro Val Lys Glu Leu Thr Phe Asp Gln Leu Gln Leu Leu Lys
395                 400                 405 ctc act cat gtg act gca ctg aaa tct aag gat cgg aaa gaa tct gtg   1480
Leu Thr His Val Thr Ala Leu Lys Ser Lys Asp Arg Lys Glu Ser Val
410                 415                 420                 425 gtt cag gag gaa aat tcc ttt tca gaa aat cag cca ttt cct tct ctt   1528
Val Gln Glu Glu Asn Ser Phe Ser Glu Asn Gln Pro Phe Pro Ser Leu
            430                 435                 440 aag atg gtt tta gag tct ttg cca gaa gat gta ggg ttt aac att gaa   1576
Lys Met Val Leu Glu Ser Leu Pro Glu Asp Val Gly Phe Asn Ile Glu
                445                 450                 455 ata aaa tgg atc tgc cag caa agg gat gga atg tgg gat ggt aac tta   1624
Ile Lys Trp Ile Cys Gln Gln Arg Asp Gly Met Trp Asp Gly Asn Leu
        460                 465                 470 tca aca tat ttt gac atg aat ctg ttt ttg gat ata att tta aaa act   1672
Ser Thr Tyr Phe Asp Met Asn Leu Phe Leu Asp Ile Ile Leu Lys Thr
475                 480                 485 gtt tta gaa aat tct ggg aag agg aga ata gtg ttt tct tca ttt gat   1720
Val Leu Glu Asn Ser Gly Lys Arg Arg Ile Val Phe Ser Ser Phe Asp
490                 495                 500                 505 gca gat att tgc aca atg gtt cgg caa aag cag aac aaa tat ccg ata   1768
Ala Asp Ile Cys Thr Met Val Arg Gln Lys Gln Asn Lys Tyr Pro Ile
            510                 515                 520 cta ttt tta act caa gga aaa tct gag att tat cct gaa ctc atg gac   1816
Leu Phe Leu Thr Gln Gly Lys Ser Glu Ile Tyr Pro Glu Leu Met Asp
                525                 530                 535 ctc aga tct cgg aca acc ccc att gca atg agc ttt gca cag ttt gaa   1864
Leu Arg Ser Arg Thr Thr Pro Ile Ala Met Ser Phe Ala Gln Phe Glu
        540                 545                 550 aat cta ctg ggg ata aat gta cat act gaa gac ttg ctc aga aac cca   1912
Asn Leu Leu Gly Ile Asn Val His Thr Glu Asp Leu Leu Arg Asn Pro
555                 560                 565 tcc tat att caa gag gca aaa gct aag gga cta gtc ata ttc tgc tgg   1960
Ser Tyr Ile Gln Glu Ala Lys Ala Lys Gly Leu Val Ile Phe Cys Trp
570                 575                 580                 585 ggt gat gat acc aat gat cct gaa aac aga agg aaa ttg aag gaa ctt   2008
Gly Asp Asp Thr Asn Asp Pro Glu Asn Arg Arg Lys Leu Lys Glu Leu
            590                 595                 600 gga gtt aat ggt cta att tat gat agg ata tat gat tgg atg cct gaa   2056
Gly Val Asn Gly Leu Ile Tyr Asp Arg Ile Tyr Asp Trp Met Pro Glu
```

|  |  |  |  |  |  |  |  | 605 |  |  |  |  | 610 |  |  |  |  | 615 |  |  |
|---|---|---|---|---|---|---|---|---|---|---|---|---|---|---|---|---|---|---|---|---|
| caa | cca | aat | ata | ttc | caa | gtg | gag | caa | ttg | gaa | cgc | ctg | aag | cag | gaa |  |  |  |  | 2104 |
| Gln | Pro | Asn | Ile | Phe | Gln | Val | Glu | Gln | Leu | Glu | Arg | Leu | Lys | Gln | Glu |  |  |  |  |  |
|  |  |  | 620 |  |  |  |  | 625 |  |  |  |  | 630 |  |  |  |  |  |  |  |
| ttg | cca | gag | ctt | aag | agc | tgt | ttg | tgt | ccc | act | gtt | agc | cgc | ttt | gtt |  |  |  |  | 2152 |
| Leu | Pro | Glu | Leu | Lys | Ser | Cys | Leu | Cys | Pro | Thr | Val | Ser | Arg | Phe | Val |  |  |  |  |  |
| 635 |  |  |  |  | 640 |  |  |  |  | 645 |  |  |  |  |  |  |  |  |  |  |
| ccc | tca | tct | ttg | tgt | ggg | gag | tct | gat | atc | cat | gtg | gat | gcc | aac | ggc |  |  |  |  | 2200 |
| Pro | Ser | Ser | Leu | Cys | Gly | Glu | Ser | Asp | Ile | His | Val | Asp | Ala | Asn | Gly |  |  |  |  |  |
| 650 |  |  |  |  | 655 |  |  |  |  | 660 |  |  |  |  | 665 |  |  |  |  |  |
| att | gat | aac | gtg | gag | aat | gct | tag | tttttattgc | acagaggtca | ttttgggggc |  |  |  |  |  |  |  |  |  | 2254 |
| Ile | Asp | Asn | Val | Glu | Asn | Ala |  |  |  |  |  |  |  |  |  |  |  |  |  |  |
|  |  |  | 670 |  |  |  |  |  |  |  |  |  |  |  |  |  |  |  |  |  | gtgcaccgct gttctgggta ttcatttttc atcactgagc attgttgatc tatgccttt 2314
gggcttctca gttcaatgaa gcaataatga agtatttaac tctttcacta cagttcttgc 2374
aagtatgcta tttaaattac ttggccaggt ataattgcca gtcagtctct ttatagtgag 2434
aaaatttatt ggttagtaat ataaatattt taaactaaat atataaatct ataatgttaa 2494
acatatgttc attaaaagca tagcactttg aaattaacta tataaatagc tcatatttac 2554
acttacagct tttcatttga tcaggtctga aatctttagc acttaaggaa aatgactatg 2614
cataattata cctgaccatg aaaaaaataa gtacctcaaa tgcatgcatt tgcactggtg 2674
attccaactg cacaaatctt tgtgccatct tgtatatagg tatttttac atgggttgac 2734
atgcacacaa caccattttc attcagtatg aaccttgagg ctgctgccat ttttccactt 2794
aaccaaacca gcctgaaggt gaacctcgaa acttgtttca taaatctttc aaaagttgtt 2854
ttacatcaat gttaaaattt caaaatgctg cagggtaatt taatgtataa aatattagta 2914
agaaaaagta tgtattgcat acttagtaga atagatcaca acatacaaat tcaattcagt 2974
gcatgcttta ggtgttaagc atgagattgt acatgtttac tgttaggtcc ttgcatctgt 3034
ggtgctaggt gagtatgaga agatgtcaag gactggacgt attttgttgc ctaaaaaaaa 3094
aaggctgttt gtaggcgttt taaatatgct tattttgtgt gtctctcact acctattaca 3154
cactgttgct ttgtgggttt gttttgtatg tgcgtgtgtt atacagtagt taaatttcca 3214
tgcagaaaaa taaatgtcct gaattttcat attagtattc tttattgtat atcatgcatg 3274
taatttattt agaaatgtag gtcttactaa atgtatatgc atgtatttca gattatacta 3334
ggatttcttg gattagaagc agattgtgtt aactgtaact taaagaatga atgttaaata 3394
aaatgataca gatttatttt cttcattaca aaatgaaatt tcaagaaggt gttacttttg 3454
tagaatggtt ttataatatg acaagaaatt ttaatatagt gtctacccta aagggatggc 3514
ttatttgcat ctacctttta ctgcatgttt ttcacaaggc agtttattca tatattgaca 3574
tattttggta gtagctgaga acctaagact tgaaattata cattgtgtag tatttttaa 3634
gctaagcaat gcaattttgg tcagatctta tttgtgtgaa gataggctct gaaatcctat 3694
ggtattgcgt ttgtaacgtt gatattaatg caaaatagtt taggaaatgg agtcttctgc 3754
aagggttctg tatactttc ccacattgta tgagattttc caaaattttg gtgtgaattg 3814
ggcactttg gaaaactcct gaaaagaat tagtttcctt catctgcaga cctttgtcca 3874
atacggttac catttctta tagtaactcg attagccata tatgtttgtt tctagtcctg 3934
ctcctttgct cctctcctat gccttccag tgctggctcc attttgaaga ctcaaggaca 3994
gaggggaagc agatcataaa gagaaaaagg agacagaaga aaggatgaag gaggaggtc 4054
atggggagtg tggcttctga gcagtttagt tgctggggag agcagacagt cactgcctac 4114

```
aatacagaca gaaccttcct gctcactttc tgtcctatct cttcctgacc ttatgaacca    4174
gtgttagtag atgattaaaa catgacaagc aatggctcct tattttcaca ggactaagtc    4234
cgggccttcg tatcactagc tgttgccttt tacaccctgc ttcagccacc ctgtccctgt    4294
cattggccct ggacttcctc tctgtgcccg tgtgtcctct gcctgggagc cctctcctcc    4354
catagtcact ttctctctgc caaactcatt tcttcttgtg cccaagacct ctctcctgag    4414
cccttgtgga aacttcagga aggatgaatc cgtctttgtg ctccacggct cgtaccttga    4474
tcaggctgtg catcacagta attctgttct aggtaggcag agttgatctt tgtctcatct    4534
gccaggctgc aggctcttca agggcaggga ccttgtcata gtcattttta ttttcacagt    4594
gcttggaaca tggtggaaaa tgaatgttgg aattattgga gtaatataat ttgtatcaaa    4654
tgtccttttg aattaagaga tttagttatg tttactaaga atgtaaactt tgaattggtt    4714
tgcattttaa caattaggat ggtttattga tgtgaatttt gaaatgtaga ggtataatgt    4774
taaattattt tatactttat ggaaatcaag tgaaatgttt gaaaaaatgc cgccattatc    4834
ctctggtatt ttctactctc tggaattatg tgctgtaaat gatcggctgt aaatgtgagg    4894
cacaccaccc acccctgtgt ggaaagtgtt gtggcgcttc ctgccaccca cccacctctc    4954
tgccgttgct ccttgtgaca cttgtctgtc gtctcccatc caaactccaa gcttacagct    5014
acctcagtac tgctttgctt gtctgaaaca cctcctttgc cttccttcag tgtcccgctc    5074
aggtgcagcc tcctccctaa agctcatctc agcttttgat ctgaatgatg atggaaacat    5134
gcagacagcc tctcagtctt actatttaat gttgtagctg gaaaaaaacc cagagaggtt    5194
aactgatata ctgggttggg actaggatgt gggttttgtg actctgaatc ccatgttctc    5254
aaactacgct gccttccgaa gtctggcatt tgttagctca tgcttccttg tagtccagct    5314
tcttatgtgc ctgttatatt ctccagtaag attgtaagcc ccttaagggc agggacgtct    5374
ttgcatctct agcactgcta tagtgttcta tccttagtta tgaactagat aaataaatgg    5434
tggtggcaac                                                          5444
```

<210> SEQ ID NO 8
<211> LENGTH: 672
<212> TYPE: PRT
<213> ORGANISM: Homo sapiens

<400> SEQUENCE: 8

```
Met Thr Pro Ser Gln Val Ala Phe Glu Ile Arg Gly Thr Leu Leu Pro
1               5                   10                  15

Gly Glu Val Phe Ala Ile Cys Gly Ser Cys Asp Ala Leu Gly Asn Trp
            20                  25                  30

Asn Pro Gln Asn Ala Val Ala Leu Leu Pro Glu Asn Asp Thr Gly Glu
        35                  40                  45

Ser Met Leu Trp Lys Ala Thr Ile Val Leu Ser Arg Gly Val Ser Val
    50                  55                  60

Gln Tyr Arg Tyr Phe Lys Gly Tyr Phe Leu Glu Pro Lys Thr Ile Gly
65                  70                  75                  80

Gly Pro Cys Gln Val Ile Val His Lys Trp Glu Thr His Leu Gln Pro
                85                  90                  95

Arg Ser Ile Thr Pro Leu Glu Ser Glu Ile Ile Asp Asp Gly Gln
            100                 105                 110

Phe Gly Ile His Asn Gly Val Glu Thr Leu Asp Ser Gly Trp Leu Thr
        115                 120                 125
```

-continued

```
Cys Gln Thr Glu Ile Arg Leu Arg Leu His Tyr Ser Glu Lys Pro Pro
    130                 135                 140

Val Ser Ile Thr Lys Lys Leu Lys Lys Ser Arg Phe Arg Val Lys
145                 150                 155                 160

Leu Thr Leu Glu Gly Leu Glu Glu Asp Asp Asp Arg Val Ser Pro
                    165                 170                 175

Thr Val Leu His Lys Met Ser Asn Ser Leu Glu Ile Ser Leu Ile Ser
                180                 185                 190

Asp Asn Glu Phe Lys Cys Arg His Ser Gln Pro Glu Cys Gly Tyr Gly
                195                 200                 205

Leu Gln Pro Asp Arg Trp Thr Glu Tyr Ser Ile Gln Thr Met Glu Pro
210                 215                 220

Asp Asn Leu Glu Leu Ile Phe Asp Phe Phe Glu Glu Asp Leu Ser Glu
225                 230                 235                 240

His Val Val Gln Gly Asp Ala Leu Pro Gly His Val Gly Thr Ala Cys
                    245                 250                 255

Leu Leu Ser Ser Thr Ile Ala Glu Ser Gly Lys Ser Ala Gly Ile Leu
                260                 265                 270

Thr Leu Pro Ile Met Ser Arg Asn Ser Arg Lys Thr Ile Gly Lys Val
            275                 280                 285

Arg Val Asp Tyr Ile Ile Ile Lys Pro Leu Pro Gly Tyr Ser Cys Asp
290                 295                 300

Met Lys Ser Ser Phe Ser Lys Tyr Trp Lys Pro Arg Ile Pro Leu Asp
305                 310                 315                 320

Val Gly His Arg Gly Ala Gly Asn Ser Thr Thr Thr Ala Gln Leu Ala
                    325                 330                 335

Lys Val Gln Glu Asn Thr Ile Ala Ser Leu Arg Asn Ala Ala Ser His
                340                 345                 350

Gly Ala Ala Phe Val Glu Phe Asp Val His Leu Ser Lys Asp Phe Val
            355                 360                 365

Pro Val Val Tyr His Asp Leu Thr Cys Cys Leu Thr Met Lys Lys Lys
        370                 375                 380

Phe Asp Ala Asp Pro Val Glu Leu Phe Glu Ile Pro Val Lys Glu Leu
385                 390                 395                 400

Thr Phe Asp Gln Leu Gln Leu Leu Lys Leu Thr His Val Thr Ala Leu
                    405                 410                 415

Lys Ser Lys Asp Arg Lys Glu Ser Val Val Gln Glu Asn Ser Phe
                420                 425                 430

Ser Glu Asn Gln Pro Phe Pro Ser Leu Lys Met Val Leu Glu Ser Leu
            435                 440                 445

Pro Glu Asp Val Gly Phe Asn Ile Glu Ile Lys Trp Ile Cys Gln Gln
450                 455                 460

Arg Asp Gly Met Trp Asp Gly Asn Leu Ser Thr Tyr Phe Asp Met Asn
465                 470                 475                 480

Leu Phe Leu Asp Ile Ile Leu Lys Thr Val Leu Glu Asn Ser Gly Lys
                    485                 490                 495

Arg Arg Ile Val Phe Ser Ser Phe Asp Ala Asp Ile Cys Thr Met Val
                500                 505                 510

Arg Gln Lys Gln Asn Lys Tyr Pro Ile Leu Phe Leu Thr Gln Gly Lys
            515                 520                 525

Ser Glu Ile Tyr Pro Glu Leu Met Asp Leu Arg Ser Arg Thr Thr Pro
530                 535                 540

Ile Ala Met Ser Phe Ala Gln Phe Glu Asn Leu Leu Gly Ile Asn Val
```

His Thr Glu Asp Leu Leu Arg Asn Pro Ser Tyr Ile Gln Ala Lys
    545                 550                 555                 560

Ala Lys Gly Leu Val Ile Phe Cys Trp Gly Asp Asp Thr Asn Asp Pro
            565                 570                 575

Glu Asn Arg Arg Lys Leu Lys Glu Leu Gly Val Asn Gly Leu Ile Tyr
        580                 585                 590

Asp Arg Ile Tyr Asp Trp Met Pro Gln Pro Asn Ile Phe Gln Val
    595                 600                 605

Glu Gln Leu Glu Arg Leu Lys Gln Glu Leu Pro Glu Leu Lys Ser Cys
610                 615                 620

Leu Cys Pro Thr Val Ser Arg Phe Val Pro Ser Ser Leu Cys Gly Glu
625                 630                 635                 640

Ser Asp Ile His Val Asp Ala Asn Gly Ile Asp Asn Val Glu Asn Ala
            645                 650                 655

660                 665                 670

<210> SEQ ID NO 9
<211> LENGTH: 25
<212> TYPE: DNA
<213> ORGANISM: artificial sequence
<220> FEATURE:
<223> OTHER INFORMATION: oligonucleotide

<400> SEQUENCE: 9
attaaccctc actaaatgct gggga                                           25

<210> SEQ ID NO 10
<211> LENGTH: 26
<212> TYPE: DNA
<213> ORGANISM: artificial sequence
<220> FEATURE:
<223> OTHER INFORMATION: oligonucleotide

<400> SEQUENCE: 10
attaaccctc actaaatcgg tcatag                                          26

<210> SEQ ID NO 11
<211> LENGTH: 25
<212> TYPE: DNA
<213> ORGANISM: artificial sequence
<220> FEATURE:
<223> OTHER INFORMATION: oligonucleotide

<400> SEQUENCE: 11
attaaccctc actaaatgct ggtgg                                           25

<210> SEQ ID NO 12
<211> LENGTH: 25
<212> TYPE: DNA
<213> ORGANISM: artificial sequence
<220> FEATURE:
<223> OTHER INFORMATION: oligonucleotide

<400> SEQUENCE: 12
attaaccctc actaaatgct ggtag                                           25

<210> SEQ ID NO 13
<211> LENGTH: 26
<212> TYPE: DNA
<213> ORGANISM: artificial sequence
<220> FEATURE:
<223> OTHER INFORMATION: oligonucleotide -continued

<400> SEQUENCE: 13
attaaccctc actaaagatc tgactg         26

<210> SEQ ID NO 14
<211> LENGTH: 25
<212> TYPE: DNA
<213> ORGANISM: artificial sequence
<220> FEATURE:
<223> OTHER INFORMATION: oligonucleotide

<400> SEQUENCE: 14
attaaccctc actaaatgct gggtg          25

<210> SEQ ID NO 15
<211> LENGTH: 25
<212> TYPE: DNA
<213> ORGANISM: artificial sequence
<220> FEATURE:
<223> OTHER INFORMATION: oligonucleotide

<400> SEQUENCE: 15
attaaccctc actaaatgct gtatg          25

<210> SEQ ID NO 16
<211> LENGTH: 25
<212> TYPE: DNA
<213> ORGANISM: artificial sequence
<220> FEATURE:
<223> OTHER INFORMATION: oligonucleotide

<400> SEQUENCE: 16
attaaccctc actaaatgga gctgg          25

<210> SEQ ID NO 17
<211> LENGTH: 25
<212> TYPE: DNA
<213> ORGANISM: artificial sequence
<220> FEATURE:
<223> OTHER INFORMATION: oligonucleotide

<400> SEQUENCE: 17
attaaccctc actaaatgtg gcagg          25

<210> SEQ ID NO 18
<211> LENGTH: 25
<212> TYPE: DNA
<213> ORGANISM: artificial sequence
<220> FEATURE:
<223> OTHER INFORMATION: oligonucleotide

<400> SEQUENCE: 18
attaaccctc actaaagcac cgtcc          25

<210> SEQ ID NO 19
<211> LENGTH: 30
<212> TYPE: DNA
<213> ORGANISM: artificial sequence
<220> FEATURE:
<223> OTHER INFORMATION: oligonucleotide

<400> SEQUENCE: 19
cattatgctg agtgatatct ttttttttaa     30

<210> SEQ ID NO 20
<211> LENGTH: 30

```
<212> TYPE: DNA
<213> ORGANISM: artificial sequence
<220> FEATURE:
<223> OTHER INFORMATION: oligonucleotide

<400> SEQUENCE: 20
cattatgctg agtgatatct ttttttttac                                        30

<210> SEQ ID NO 21
<211> LENGTH: 30
<212> TYPE: DNA
<213> ORGANISM: artificial sequence
<220> FEATURE:
<223> OTHER INFORMATION: oligonucleotide

<400> SEQUENCE: 21
cattatgctg agtgatatct ttttttttag                                        30

<210> SEQ ID NO 22
<211> LENGTH: 30
<212> TYPE: DNA
<213> ORGANISM: artificial sequence
<220> FEATURE:
<223> OTHER INFORMATION: oligonucleotide

<400> SEQUENCE: 22
cattatgctg agtgatatct ttttttttca                                        30

<210> SEQ ID NO 23
<211> LENGTH: 30
<212> TYPE: DNA
<213> ORGANISM: artificial sequence
<220> FEATURE:
<223> OTHER INFORMATION: oligonucleotide

<400> SEQUENCE: 23
cattatgctg agtgatatct ttttttttcc                                        30

<210> SEQ ID NO 24
<211> LENGTH: 30
<212> TYPE: DNA
<213> ORGANISM: artificial sequence
<220> FEATURE:
<223> OTHER INFORMATION: oligonucleotide

<400> SEQUENCE: 24
cattatgctg agtgatatct ttttttttcg                                        30

<210> SEQ ID NO 25
<211> LENGTH: 30
<212> TYPE: DNA
<213> ORGANISM: artificial sequence
<220> FEATURE:
<223> OTHER INFORMATION: oligonucleotide

<400> SEQUENCE: 25
cattatgctg agtgatatct ttttttttga                                        30

<210> SEQ ID NO 26
<211> LENGTH: 30
<212> TYPE: DNA
<213> ORGANISM: artificial sequence
<220> FEATURE:
<223> OTHER INFORMATION: oligonucleotide

<400> SEQUENCE: 26
```

```
cattatgctg agtgatatct ttttttttgc                                30

<210> SEQ ID NO 27
<211> LENGTH: 30
<212> TYPE: DNA
<213> ORGANISM: artificial sequence
<220> FEATURE:
<223> OTHER INFORMATION: oligonucleotide

<400> SEQUENCE: 27
cattatgctg agtgatatct ttttttttgg                                30

<210> SEQ ID NO 28
<211> LENGTH: 22
<212> TYPE: DNA
<213> ORGANISM: artificial sequence
<220> FEATURE:
<223> OTHER INFORMATION: oligonucleotide

<400> SEQUENCE: 28
tttcaaaatg ctgcagggta at                                        22

<210> SEQ ID NO 29
<211> LENGTH: 22
<212> TYPE: DNA
<213> ORGANISM: artificial sequence
<220> FEATURE:
<223> OTHER INFORMATION: oligonucleotide

<400> SEQUENCE: 29
acccacaaag caacagtgtg ta                                        22

<210> SEQ ID NO 30
<211> LENGTH: 24
<212> TYPE: DNA
<213> ORGANISM: artificial sequence
<220> FEATURE:
<223> OTHER INFORMATION: oligonucleotide

<400> SEQUENCE: 30
cacaatctgc ttctaatcca agaa                                      24

<210> SEQ ID NO 31
<211> LENGTH: 22
<212> TYPE: DNA
<213> ORGANISM: artificial sequence
<220> FEATURE:
<223> OTHER INFORMATION: oligonucleotide

<400> SEQUENCE: 31
tgctttgtgg gtttgtttg ta                                         22
```